United States Patent [19]

Dorval et al.

[11] Patent Number: 5,547,833
[45] Date of Patent: Aug. 20, 1996

[54] RADIAL FLOW ASSAY, DELIVERING MEMBER, TEST KIT, AND METHODS

[75] Inventors: Brent L. Dorval, Douglas; Lilibeth K. Denham, Cambridge; Alexander M. Klibanov, Newton, all of Mass.

[73] Assignee: Intracel Corporation, Cambridge, Mass.

[21] Appl. No.: 177,733

[22] Filed: Jan. 4, 1994

[51] Int. Cl.⁶ ........................ G01N 33/569; G01N 33/543
[52] U.S. Cl. .................. 435/5; 210/483; 210/488; 210/500.29; 210/506; 422/56; 422/57; 422/58; 422/61; 435/805; 435/810; 435/970; 435/975; 436/169; 436/170; 436/518; 436/528; 436/530; 436/531; 436/536; 436/805; 436/810
[58] Field of Search .................. 210/483, 488, 210/500.29, 506; 422/56–58, 61; 435/5, 805, 810, 970, 975; 436/518, 528, 530–532, 169, 170, 805, 807, 809, 810

[56] References Cited

U.S. PATENT DOCUMENTS

| | | | |
|---|---|---|---|
| 4,066,403 | 1/1978 | Bruschi | 436/170 |
| 4,248,829 | 2/1981 | Kitajima et al. | 422/56 |
| 4,366,241 | 12/1982 | Tom et al. | 422/56 |
| 4,373,932 | 2/1983 | Gribnau et al. | |
| 4,407,943 | 10/1983 | Cole et al. | |
| 4,469,787 | 9/1984 | Woods et al. | |
| 4,472,508 | 9/1984 | Ingbar | |
| 4,474,877 | 10/1984 | Imagawa et al. | |
| 4,604,208 | 8/1986 | Chu et al. | |
| 4,632,901 | 12/1986 | Valkirs et al. | 422/56 |
| 4,670,381 | 6/1987 | Frickey et al. | 422/56 |
| 4,727,019 | 2/1988 | Valkirs et al. | 435/5 |
| 4,757,002 | 7/1988 | Joo | |
| 4,780,422 | 10/1988 | Mitani et al. | |
| 4,803,171 | 2/1989 | Baier et al. | 435/805 |
| 4,808,529 | 2/1989 | Doppelfeld et al. | 435/14 |
| 4,829,012 | 5/1989 | Cambiaso et al. | |
| 4,874,813 | 10/1989 | O'Shannessy | 530/816 |
| 4,912,034 | 3/1990 | Kalra et al. | |
| 4,952,519 | 8/1990 | Lau | 435/180 |
| 4,956,302 | 9/1990 | Gordon et al. | 436/162 |
| 4,962,023 | 10/1990 | Todd et al. | 436/531 |
| 5,008,078 | 4/1991 | Yaginuma et al. | 422/56 |
| 5,093,230 | 3/1992 | Osther et al. | 435/7.9 |
| 5,169,789 | 12/1992 | Bernstein | 422/56 |
| 5,191,066 | 3/1993 | Bieniarz et al. | |
| 5,202,267 | 4/1993 | Ditlow et al. | 422/58 |
| 5,206,136 | 4/1993 | Monji et al. | |
| 5,217,905 | 6/1993 | Marchand et al. | 422/56 |
| 5,252,459 | 10/1993 | Tarcha et al. | |
| 5,286,452 | 2/1994 | Hansen | |
| 5,308,580 | 5/1994 | Clark | |

FOREIGN PATENT DOCUMENTS

| | | |
|---|---|---|
| 0152305 | 8/1985 | European Pat. Off. |
| 0299359 | 1/1989 | European Pat. Off. |
| 0308232 | 3/1989 | European Pat. Off. |
| 430517A2 | 6/1991 | European Pat. Off. |
| 0537827 | 4/1993 | European Pat. Off. |
| 2204398 | 11/1988 | United Kingdom |

OTHER PUBLICATIONS

Johnstone, A. and Thorpe, R., Immunochemistry in Practice, Boston: Blackwell Scientific Publications, 1987, pp. 214–225.
Tijssen P., Practice & Theory of Enzyme Immunoassays, Laboratory Techniques in Biochemistry and Molecular Biology, vol. 15, New York: Elsevier, 1985, pp. 329–349.
Millipore Direct Catalog (1991–1992), pp. 16–18.
Micro Filtration Systems Catalog (1981), pp. 14–15.
Websters Ninth New Collegiate Dictionary, Merriam–Webster Inc., Springfield, Mass., 1990, p. 618.

Primary Examiner—James C. Housel
Assistant Examiner—Christopher L. Chin
Attorney, Agent, or Firm—Wolf, Greenfield & Sacks, P.C.

[57] ABSTRACT

A delivering member for filtering and delivering a sample to a test assay surface includes a prefilter having a sample receiving surface and a surface for delivering a sample to a test assay surface. The prefilter includes a diffusing material on its receiving surface for rapidly and evenly diffusing a sample across the prefilter receiving surface. In this way, a sample may be rapidly and evenly delivered to a test assay surface. A test assay solid phase has a surface including an area carrying an immobilized species and an area free of immobilized species. When a sample is applied to the surface, followed by application of a labeled species, the evenness of distribution of the labeled species is indicative of the evenness of application of the sample. A kit includes a delivering member and an assay surface.

6 Claims, 4 Drawing Sheets

DISEASE

NO DISEASE

RADIAL FLOW ASSAY, DELIVERING MEMBER, TEST KIT, AND METHODS

This application is being filed concurrently with a commonly-owned U.S. Patent Application entitled "Assay Employing Both Protein and Antibody", by Dorval et al., which is incorporated herein by reference for all purposes.

FIELD OF THE INVENTION

The present invention relates generally to assay reageants, methods, and apparatus, and more particularly to radial flow assay apparatus and methods providing rapid and sensitive determination of an analyte in a variety of test assays.

BACKGROUND OF THE INVENTION

Immuncassays can be used to detect the presence of unwanted agents in a sample of fluid, for example the presence of bacteria in a bodily fluid or a pollutant in water. They can be used also to test for the presence of antibodies in body fluids, as an indication of the presence of an infectious agent, a cancer cell or an autoimmune disease.

A variety of test assay components have been developed for use in immunoassavs, and some of these components exploit the capillary flow of fluid through a porous medium. Assays utilizing this phenomenon have occasionally been somewhat improperly termed "chromatographic assays", and some involve but a one-step procedure. For example, U.S. Pat. No. 4,956,302, issued Sep. 11, 1990 to Gordon et al., describes an assay device including a chromatographic medium having a reaction site at which a specific binding reagent is immobilized, a sample application well located adjacent to the chromatographic medium and offset upstream from the reaction size, and a liquid absorption blotter offset downstream from the reaction site. A fluid sample is applied to the application well and is transported through the chromatographic medium, through the reaction site, and to the blotter. The reaction site is then contacted with a labeled, specific binding material, is washed to remove unbound species, and the label is detected.

U.K. Patent Application Number 8809867, published Nov. 9, 1988 under Publication Number 2204398A, describes a nitrocellulose medium including a sample application area, non-immobilized, labeled binding reagent specific for a first analyte epitope located downstream therefrom, and immobilized, non-labeled binding reagent specific for a second analyte epitope located further downstream. The analyte is provided in a fluid which carries the analyte to the labeled reagent and which carries the analyte and labeled reagent together to the immobilized, non-labeled reagent. After the assay, observation of label at the zone of immobilization is indicative of the presence of analyte in the sample.

in each of the above-described devices, the chromatographic medium provides the function of filtering the fluid sample of unwanted particulates, and of slowing the flow of fluid to allow specific bindlng to occur and to efficiently carry non-immobilized reagents to sites where other reagents are immobilized. However, this slow flow contributes to non-specific binding as well, and one must wait for a period of time on the order of minutes for a test result.

Filtration of large quantities of serum and blood has also been carried out using porous media such as nitrocellulose. However, a significant pressure differential must be applied across a nitrocellulose filter to achieve such filtration.

Porous media have been used to form so-called "prefilters" in test assay apparatus, these prefilters being used to spread a sample from a localized application area over a larger test assay surface area. U.S. Pat. No. 4,912,034, issued Mar. 27, 1990 to Kalra et al. describes such a prefilter. These prefilters are typically constructed of glass fibers, and provide rapid wetting of a test assay surface, but provide poor filtration, as selection of a prefilter having a pore size providing adequate filtration generally slows the wetting process significantly. That is, to apply a sample using a prior art prefilter, good filtration and rapid wetting of an assay surface are generally mutually exclusive. Additionally, glass fibers have very large void (retention) volumes, hence they absorb significant quantities of sample. Therefore, if only a small sample is available, it must be diluted significantly if the assay surface is to be adequately wetted. Then, to boost sensitivity, an enzymatic tag is typically employed.

Although many such assays represent extraordinary improvements over one prior methodology for determining the presence of an agent in a sample, the goal remains to develop immunoassays that are rapid and sensitive. It is a drawback of almost every immunoassay presently in use that the assay either is too slow (5–30 minutes) or, if faster, is not sufficiently sensitive (or both). Where the detection of disease is concerned, it is unacceptable to compromise on sensitivity, and accordingly those assays that are among the most sensitive tend to be cumbersome and slow.

SUMMARY OF THE INVENTION

The present invention is directed to products and processes that are useful in a variety of test assays. The invention permits the detection of analytes in very small samples, with enhanced sensitivity. The invention also permits the rapid detection of analytes in a sample. It further eliminates many steps characteristic of prior art assays, including in particular wash steps. The foregoing is accomplished, generally, by rapidly dispersing the sample into a film, and then delivering this film uniformly to a test assay surface.

Thus, according to one aspect of the invention, a delivering member for delivering a sample to a test assay surface is provided. The delivery member includes a prefilter having a sample receiving surface. The prefilter also includes a sample delivering surface for delivering the sample to the test assay surface. A diffusing material is provided on the prefilter sample receiving surface for rapidly and laterally dispersing the sample when applied to the delivering member. According to a preferred embodiment the delivering member is substantially circular, and a sample is applied to the center of the receiving surface. Then the sample is rapidly dispersed radially from the location of sample application.

The diffusing material can be, for example, a membrane or a surfactant. Thus, the delivering member may be prepared from a pair of membranes in face to face relation, one of the membranes acting as the diffusing material and the other being the prefilter. The diffusing membrane has a porosity and thickness selected to rapidly laterally diffuse a fluid sample over the prefilter receiving surface. The prefilter is a substantially planar membrane having a porosity and thickness selected to rapidly transfer the sample from the receiving surface to the delivering surface while filtering the sample of particulate material larger than a predetermined dimension. In one arrangement, the diffusing material is a membrane having a pore size of about 5–25 microns and the prefilter is a membrane having a pore size of from about 0.1 micron to 1.0 microns and a thickness of from about 50 microns to about 300 microns.

If the diffusing material is a surfactant, then the construction of the delivery member may be according to a wide variety of embodiments, discussed in greater detail below. In any event, the delivering membrane is constructed and arranged preferably such that the sample is rapidly and laterally diffused over The prefilter receiving surface, and then delivered evenly and uniformly to the test assay surface.

According to another aspect of the invention, a method for making a delivering member for delivering a sample to a test assay surface is provided. A porous, substantially planar prefilter having a sample receiving surface is provided. A diffusing material then is applied To the sample receiving surface. The diffusing material can be a diffusing membrane having a periphery and having a porous structure providing rapid lateral flow of a sample applied to the receiving surface. In this instance, the diffusing membrane is mounted on the prefilter in face to face relation, preferably by a connector about the periphery of the prefilter and diffusing membrane.

According to another aspect of the invention, a method of delivering a sample to a test assay surface is provided. A delivering surface of a prefilter is held in even contact with a test assay surface. A fluid sample then is applied to a diffusing material on a receiving surface of the prefilter so as to cause rapid lateral flow of the fluid sample at the receiving surface. The fluid sample then permeates the prefilter in a direction perpendicular to the direction of the lateral flow. In other words, the sample first flows in a direction parallel to the plane defined by the receiving surface and the test assay surface, and then flows through the prefilter and onto the test assay surface in a direction perpendicular to the first direction.

According to another aspect of the invention, a test assay kit for the determination of an analyze is provided. The test assay kit is a package containing a test assay solid phase having a test assay surface carrying an immobilized binding partner of an analyze. The package also contains a prefilter having a sample receiving surface and a sample delivering surface positionable in face to face relation with the test assay surface, and being removable therefrom, with a diffusing material on the sample receiving surface. The package also contains an urging member for holding the prefilter delivering surface and the test assay surface in even contact. The urging member can be an absorbent material in contact with a test assay solid phase. Most preferably the prefilter is a planar cellulosic membrane, the diffusing material is a substantially planar cellulosic membrane and the test assay surface is a surface of a planar membrane, and the test assay surface has pores of a dimension larger than the analyte and the delivering member has pores smaller than those of the assay surface. The package further may contain detection reagents as described herein, including labeled detection reagents. The detailed construction of the delivering member may be as described above the kit may also contain instruction for applying a predetermined amount of sample to the delivering member.

According to another aspect of the invention, a test assay kit for the determination of an analytes is provided. The kit comprises a package containing a test assay surface for supporting a test assay reaction and a porous cellulosic prefilter having a pore size of from about 0.1 to about 1.0 microns, and having a delivering surface positionable in face to face relation with the test assay surface.

According to still another aspect of the invention, a method of making a test assay kit for the determination of an analyte is provided. The method involves immobilizing a binding partner of an analyte on a test assay surface; fabricating a delivering member by applying a diffusing material to a sample receiving surface of a substantially planar prefilter; and providing an urging member positionable so as to hold the delivering surface in even contact with a test assay surface. The test assay surface, delivering member and urging member then are packaged together to form the kit. The urging member can be positioned, prior to packaging the materials, in contact with one of the porous delivering member or the assay solid phase so as to hold the delivering surface in even contact with the assay surface. the method may also include formulating a detection reagent containing a labeled binding partner of the analyte.

According to another aspect of the invention, a test assay method for the determination of an analyte is provided. A fluid sample suspected of containing the analyte is applied to a receiving surface of the porous delivering member also having a delivering surface in even contact with a test assay surface. The fluid sample is caused to first rapidly flow laterally. The fluid sample then is caused to permeate the delivering member and to be evenly transferred to the test assay surface.

According to another aspect of the invention, a test assay method for the determination of an analyte is provided. A fluid sample suspected of containing an analyte is applied to a diffusing material on a receiving surface of a porous delivering member. The porous delivering member also includes a delivering surface in even contact with a test assay surface carrying an immobilized binding partner of an analyte. The fluid sample is thus caused to rapidly and laterally flow in a direction substantially parallel to the receiving surface. The fluid sample then is allowed to permeate the delivering member and to be transferred evenly to the test assay surface. The delivering member then is removed from the test assay surface. The test assay surface is contacted with a detection reagent containing one of the labeled binding partner of the analyte or a labeled binding partner of the immobilized binding partner. Then the label is detected. Preferably, the test assay surface has pores of the dimension larger than the analyte and the delivering member has pores of a dimension larger than those of the test assay surface.

According to another aspect of the invention, a test assay method for the determination of an analyte is provided. A sample is applied to a test assay surface having regions capable of non-specific binding. The sample includes blocking species in an amount to only partially block the regions. The regions then are contacted with a detection reagent including a species carrying a label. Then, the uniformity of the distribution of non-specific binding of the labeled species is measured, the uniformity being determinative of the evenness of the application of the sample to the test assay surface. Preferably, the regions are free of any immobilized biological reagents.

According to another aspect of the invention, a test assay solid phase having a test assay surface is provided. The test assay solid phase may be used in accordance with the method of the invention described immediately above. The test assay surface includes an area having a chemical functionality that allows non-specific binding of labeled reagent to a degree indicative of the extent of sample first applied to the area. Thus, when a sample is first applied to the area to a particular extent, followed by application of the labeled reagent, labeled reagent is present to a particular degree.

When sample is first applied to the area to a second extent different from the first extent, followed by application of labeled reagent, labeled reagent non-specifically binds to the area to a second degree distinguishable from the first degree. The test assay solid surface may include a second area carrying an immobilized binding partner of an analyte.

According to another aspect of the invention, a method of delivering a fluid sample to a test assay surface is provided. The method includes the steps of holding a delivering surface of a prefilter in even contact with a test assay surface, forming a film of the fluid sample on a receiving surface of the prefilter, and allowing the film to permeate the prefilter and to evenly wet the test assay surface.

According to still another aspect of the invention, an improvement to immunoassays including kits and devices employing prefilters is provided. The improvement involves in one aspect the use of a prefilter having a pore size of from about 0.1 to 1.0 microns. The improvement in another aspect involves a prefilter comprising a pair of membranes in face To face relation. The improvement in another aspect involves a prefilter having a sample receiving surface, and constructed and arranged to rapidly laterally diffuse a fluid sample over the receiving surface and to then allow the sample to permeate the prefilter and to be delivered uniformly and evenly to a test assay surface. The improvement in still another aspect involves a prefilter having a sample receiving surface and a surface for delivering the sample to the test assay surface, and a diffusing material on the prefilter sample receiving surface. These and other aspects of the invention will be described in greater detail below in connection with the drawings.

DETAILED DESCRIPTION OF THE PREFERRED EMBODIMENTS

Many pairs of biological species exhibit mutual affinity, or mutual binding capacity, typically defined by specific or non-specific binding or interaction. Such interaction generally occurs between pairs of molecular species in which one member possesses one or more particular exposed areas which bind to one or more particular exposed areas of the other member of the pair. The exposed areas allowing such binding are typically defined by specific spatial and/or polar organization. The term "binding partners" may be used, and is used herein, to define pairs of species exhibiting such mutual affinity. For example, such binding partners include antibody/antigen, antibody/hapten, enzyme/substrate, enzyme/inhibitor, enzyme/cofactor, biotin/avidin, binding protein/substrate, carrier protein/substrate, lectin/carbohydrate, receptor/hormone, receptor/effector, complementary strands of nucleic acid, repressor/inducer, and the like.

In many test assays, it is desirable to capture, or determine, an analyte defined by one member of a pair of biological species exhibiting mutual affinity. Many immunoassays have been developed which are designed to capture such an analyte, for example to capture an antibody produced by an animal in response to an antigen. According to one such immunoassay, the antigen is immobilized on a test assay surface, a serum sample is contacted by the test assay surface so that antibodies specific for the immobilized antigen are captured at the surface, and a detection reagent including a labeled binding partner of the analyte antibody is then contacted with the test assay surface so that the presence of the analyte is indicated by label immobilized at the surface.

The present invention provides test assays that are rapid, sensitive and useful with small sample sizes. It provides in particular a delivering member for filtering, and rapidly and evenly delivering an assay sample to a test assay surface. Additionally, a test assay solid phase is provided, the assay solid phase exposing a test assay surface selected so as to provide advantageous measurement of the evenness of distribution of a sample over the surface.

As used herein, the term "sample" is meant to define a fluid mixture or solution suspected of carrying an analyte to be determined by a test assay. When components of the present invention are used in a biological assay, the sample will generally be delivered as an aqueous solution or suspension. The delivering member and test assay surface may, together, be included in a test assay kit in accordance with another embodiment of the invention, and these two components are illustrated in FIG. 1.

Figure 1:
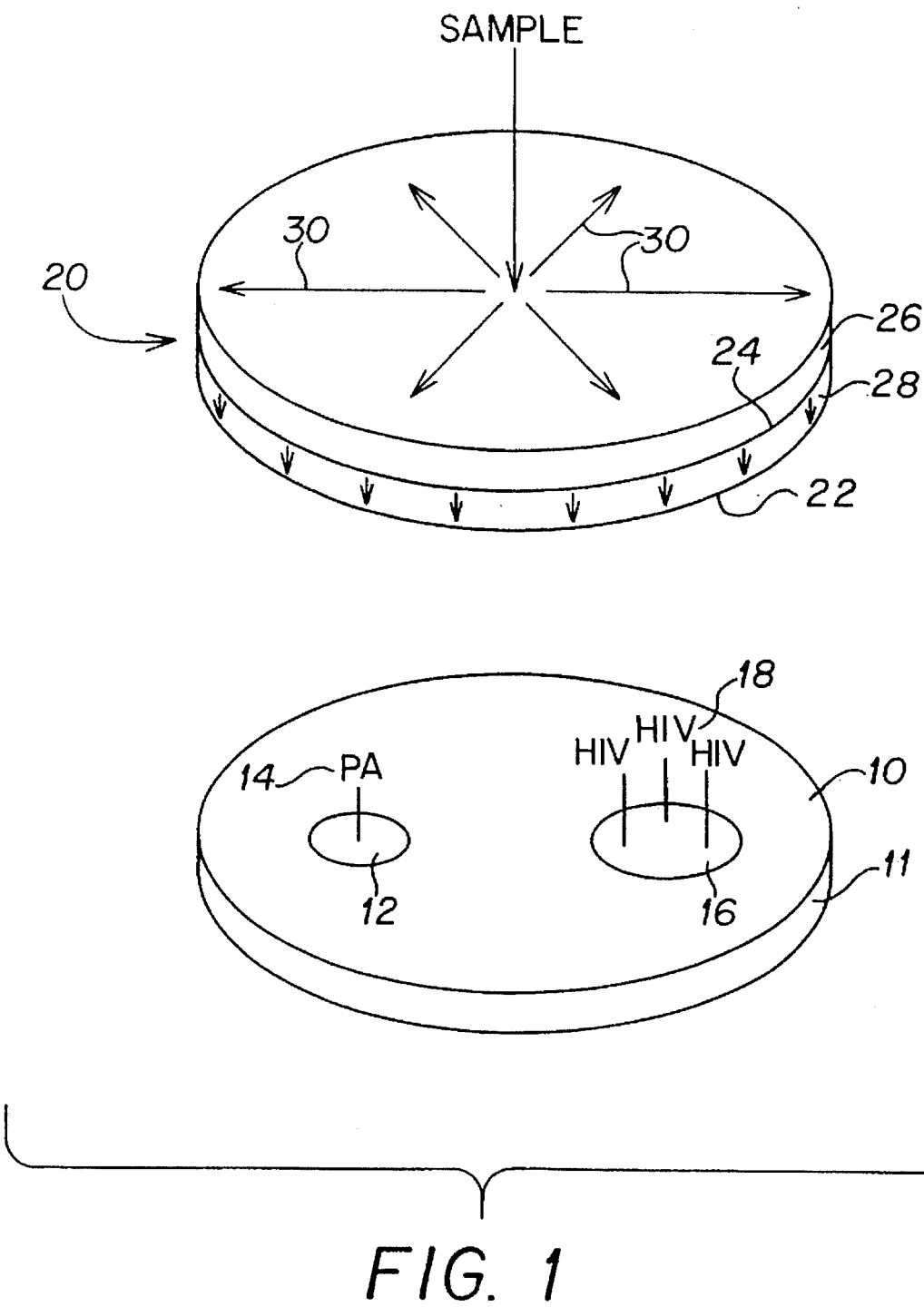
FIG. 1 illustrates a delivering member and a test assay solid phase including a test assay surface according to one embodiment of the present invention.

Referring to FIG. 1, a porous delivering member in accordance with the invention is illustrated at 20, and is comprised of prefilter 28 which has a sample receiving surface 24 and a sample delivering surface 22. A diffusing material 26 is provided on receiving surface 24 of prefilter 28. Test assay solid phase 11 includes test assay surface 10, and delivering surface 22 of prefilter 28 is conformable to test assay surface 10. Prefilter 28 and test assay solid phase 11 are substantially planar according to the embodiment illustrated, but need not be it is important only that delivering member 20 is constructed so as to evenly wet test assay surface 10 with a fluid sample, and this may be achieved if delivering surface 22 and test assay surface 10 are of conforming shape, and/or if delivering surface 22 and test assay surface 10 are conformable to each other.

Prefilter 28 and, optionally, assay solid phase 11 are constructed of a matrix having a porous structure that is inert with respect to sample components, detection reagents or other species with which these elements come into contact during a test assay, or is capable of being made inert. As used herein, the term "inert" refers to a chemical or biological state in which the material does not interact with any component in a test sample in the manner in which any binding partner pairs in the assay interact, or act to hinder any desired assay reactions. When any test assay components non-specifically bind to material defining prefilter 28 and assay solid phase 11, it is a feature of the invention that the degree of such non-specific binding is small in comparison to the degree of specific binding which is exploited by assays performed in accordance with the invention to determine analytes in a fluid sample. As discussed more fully below, it is desirable that a certain degree of labeled reagent non-specifically binds to test assay solid phase in accordance with one aspect of the invention.

Additionally, the material used to construct prefilter 28, and preferably assay solid phase 11, exhibits capillarity when exposed to the assay fluid medium, and the capacity for fluid transport of non-immobilized reagents and sample components. The term "capillarity" defines a relationship between a porous material and an assay sample fluid medium in which the contact angle between the fluid medium of the sample and the material is acute, or, a relationship in which the fluid sample is drawn through the material irrespective of the force of gravity on the fluid sample.

Exemplary materials suitable for use as prefilter 28 and, optionally, test assay solid phase 11 include woven and non-woven fibrous materials used for paper chromatography, microporous or microgranular thin layer chromatography substrates, porous polymeric materials including polyalkenes such as polyethylene and polypropylene; polyvinyl chloride; polyamides such as nylons; polyaryls such as polystyrene; polyarylsolfones; polyvinyl and polyvinylidene halides; polyvinyl and polyvinylidene alcohol; polycarbonate; polysaccharides including cellulosics such as cellulose acetate butyrate and nitrocellulose; polyesters such as polyethylene terephthalate; polyimides and pollrurethanes such as polyether polyurethanes and combinations thereof, optionally pre-treated (in the case of solid phase 11) so as to provide binding capability as described in U.S. Pat. No. 4,757,014, issued Jul. 12, 1988, and incorporated herein by reference; cellulose hydrates, charge-modified microporous membranes such as those described in U.S. Pat. No. 4,604,208, issued Aug. 5, 1986, and incorporated herein by reference; fluorinated polymeric species such as polytetrafluoroethylene and polyvinylidene fluoride; porous acrylic polymers including polyacrylates such as polymethyl methacrylate; porous so-called biomosaic polymers, that is, polymers formed from a polymerized emulsion of at least one polymerizable monomer polymerized in the presence of a biologically active material, such as are described in EP application No. 90312532.6, published under publication No. 0430517A2 on Jun. 5, 1991, incorporated herein by reference; silica; alumina; diatomaceous earth; magnesium sulfate or other inorganic finely divided material conveniently substantially uniformly disbursed in a porous polymer matrix; cloth, both naturally occurring and synthetic; agarose; dextran; gelatin, and the like. Exemplary materials suitable for use as prefilter 28 may also be found in U.S. Pat. No. 4,366,241, issued Dec. 28, 1982 to Tom et al., and incorporated herein by reference. A variety of microporous membranes suitable for use as prefilter 28 and, optionally, assay solid phase 11 are available commercially from Amicon, Geleman, Millipore, Schleicher and Schuell, and Pall Corporation.

According to one embodiment of the invention, diffusing material 26 on receiving surface 24 of prefilter 28 is a surfactant. As used herein, the term "surfactant" is defined as any species which may be attached to or coated onto receiving surface 24, and which results in a depression in the surface tension, or interfacial tension, of a fluid sample applied to receiving surface 24. Thus, the term encompasses wetting agents and emulsifiers, including detergents. A surfactant may be selected to chemically bind to receiving surface 24, or to coat surface 24 in an adsorptive manner. Secure chemical attachment of the surfactant to receiving surface 24 may optionally be effected by heating the prefilter for an appropriate period of time, or other known chemical or physical methods. Although it may be advantageous to select a surfactant to firmly bind to receiving surface 24 so as not to be dissolved in or otherwise swept away be a sample passed through prefilter 28, this is not strictly necessary. If a one-use, or disposable, prefilter is selected, then the degree to which the surfactant is removed during application of the sample is not critical so long as the surfactant serves To rapidly diffuse the sample laterally across receiving surface 24, and does not interfere with the reactivity or detection in the assay. A surfactant may permeate into prefilter 28 beyond receiving surface 24 somewhat, although it is preferable that the surfactant reside substantially at receiving surface 24.

A wide variety of surfactants may be selected for employment as diffusing material 26 of delivering member 20 of the present invention, selected from a variety of classes, including but not limited to alkyl sulfates and quaternaries, including heterogeneous polyoxyethylenes, glucamides, digitonin, bile acids, sulfo betaines, betaines, alkyldimethylamine oxides, alkyl glucosides, alkyl maltosides, lecithins and lysolecithins, homogeneous polyoxyethylenes, and alkyl thioglucosides. Specifically, polyethylene glycol dodecyl ether, octanoyl-N-methylglucamide, nonanoyl-N-methylglucamide, decanoyl-N-methylglucamide, nonyl glucoside, nonaethylene glycol octylphenyl ether, octyl glucoside, octyl thioglucoside, polyethylene polypropylene glycol, monosodium taurocholic acid, sodium taurodesoxycholate, nonaethylene glycol mono-dodecyl ether, nonaethylene glycol octylphenol ether, nonaethylene glycol octylcyclohexyl ether, heptaethyiene glycol octylphenyl ether, heptaethylene glycol octyicyciohexyl ether, polyoxyethylene sorbitan monolaurate, polyoxyethylene sorbitan monooleate, n-oczylsulfobetaine, n-decylsulfobetaine, n-dodecylsulfobetaine, n-tetradecylsulfobetaine, n-hexadecylsulfobetaine, N,N,bis(3-D-gluconamidopropyl) cholamide, polyoxyethylene lauryl ether, octaethylene glycol monododecyl ether, nonaethylene glycol monododecyl ether, cetrimmonium bromide, 3-[(3-cholamidopropyl) dimethylammonio]-1-propanesulfonate, 3-[(3-cholamidopropyl) dimethylammonio]-2-hydroxypropane-1-sulfonate, cholic acid (monosodium salt), decyl glucoside, decyl maltoside, N,N-bis (3-D-gluconamidopropyl)deoxycholamide, deoxycholic acid (sodium salt), digitin, dodecyl maltoside, N-Dodecyl-N,N-dimethylglycine, dioctyl sodium sulfosuccinate, lauryldimethylamine oxide, decaoxyethylene monolauryl ether, octaethylene glycol isotridecyl ether, polyoxyethylene isotridecyl ether, glycocholic acid (sodium salt), glycodeoxycholic acid (sodium salt), heptyl glucoside, hexyl glucoside, heptyl thioglucoside, N,N-Dimethyl-N-dodecyiamine oxide, sodium lauryl sulfate, and equivalent surfactants may be selected. A variety of suitable surfactants are sold under the trademarks TRITON, TWEEN, ZWITTERGENT, MEGA, PLURONIC, GENAMINIOX, GENAPOL, available from Calbiochem CorporaEion, La Jolla, Calif.

When a surfactant is selected as diffusing material 26, it is generally advantageous to position delivering member 20 with receiving surface facing upward during its use in a test assay procedure, that is, substantially parallel to the ground. In this way, The sample is assured of diffusing equally in all directions a radial manner. Alternatively, the delivering member may be held in non-parallel relation with the ground, and the sample may be added to a location of the receiving surface other than at the center, so that diffusion across the receiving surface is aided by gravity.

When delivering member 20 in accordance with the present invention is constructed of a surfactant as diffusing material 26 at receiving surface 24 of prefilter 28, it is to be understood that the diffusing material/prefilter combination may be arranged in one of a number of ways. According to one, the diffusing material is defined by a surfactant that coats only receiving surface 24 of prefilter 28, while the remainder of prefilter 28 is free of any surfactant. According to another, a first surfactant, or blocking agent, may coat some or all portions of the porous network of prefilter 28, while a second surfactant coats receiving surface 24 and defines diffusing material 26. According to this arrangement, zhe presence of the second surfactant at receiving surface 24 depresses The surface tension of a fluid sample applied to the prefilter relative to the remainder of the prefiltero For example, the second surfactant may be a better wetting agent than the first surfactant or may be applied in a greater amount. According to another arrangement, a surfactant coats any or all portions of prefilter 28, and the same surfactant is provided in excess at receiving surface 24, such that the surface tension of a fluid sample is depressed to a greater extent at receiving surface 24 than at other portions of prefilter 28. According to yet another arrangement, a surfactant coats receiving surface 24 and the same or another surfactant may coat other portions of prefilter 28, but the surfactant coated receiving surface 24 is separated from any surfactant coating any other region of prefilter 28 by at least a portion of prefilter 28 remaining free of surfactant. For example, receiving surface 24 may be coated with a first surfactant, and delivering surface 22 may be coated with the same or another surfactant, while portions of prefilter 28 between receiving surface 24 and delivering surface 22 remain free of any surfactant. Thus, when diffusing material 26 is defined by a surfactant, one or more surfactants may be applied to one or more portions of prefilter 28, so long as delivering member 20 is constructed and arranged such that the surface tension of a fluid sample is depressed at receiving surface 24 to a greater extent than it is depressed at portions of prefilter 28 immediately adjacent to receiving surface 24, whereby a sample will be rapidly laterally distributed prior to reaching the test assay surface.

According to another embodiment of the invention, diffusing material 26 on receiving surface 24 of prefilter 28 is a porous, inert matrix possessing capillarity with respect to an applied sample, preferably a porous membrane selected to rapidly laterally diffuse a fluid sample over receiving surface 24 via capillary action, and according to this embodiment reference will be made to diffusing material 26 as diffusing membrane 26. Diffusing membrane 26 may be fabricated from one of or a combination of the materials described above with respect to fabrication of prefilter 28. Additionally, a frit such as a glass or nylon frit material may be used. Diffusing membrane 26 and prefilter 28 may or may not be fabricated from the same material in a single delivering member 20.

Diffusing membrane 26 may be juxtaposed with receiving surface 24 of prefilter 28 by a variety of methods, for example via chemical or physical binding, such as with adhesive, preferably applied in very small, isolated regions between the membranes, or such as via stitching or microrivets or the like. Preferably, delivering member 20 includes a connector, such as a label or tab (not shown in FIG. 1), connected to the periphery of prefilter 28 and to the periphery of diffusing membrane 26, holding the diffusing membrane in face to face relation with receiving surface 24 of the prefilter. As used herein, the phrase "face to face relation" is meant to define close and juxtaposed relation, but not necessarily even contact. As used herein, the phrase "even contact" is meant to define a relationship in which a surface of one component is urged into contact with a surface of another component with application of a constant force, such as with a resilient member, so that the two surfaces evenly contact each other across the entire operative area between them defined by each surface. When membranes of the present invention are held in face to face relation, they may be brought into even contact with application of an external force, other than the force of gravity, onto one or both membranes. As will be apparent, diffusing membrane 26 and receiving surface 24 can be held in even contact during transfer of a fluid sample to assay surface 10 by delivering member 20, but need not be at other times.

To achieve rapid lateral diffusion of a fluid sample over prefilter receiving surface 24, using diffusing membrane 26, a variety of factors can be considered in the selection of diffusing membrane 26 and prefilter 28. Some of these factors include porosity, capillarity, void volume, thickness, and wetability. As used herein, the term "porosity" is meant to define characteristics of the porous structure of a membrane including pore size, directional pore orientation, the degree of pore blockage or openness, and the like. As one example of a suitable combination of a membrane selected as diffusing membrane 26 and a membrane selected as prefilter 28, both membranes may be constructed of the same material, with diffusing membrane 26 being selected to have a pore size larger than that of prefilter 28. According to this arrangement, and with reference to FIG. 1, application of a sample at the center of diffusing member 26 will result in rapid permeation of the fluid sample laterally through membrane 26. Such rapid lateral diffusion is due in part to the relatively large pore size and resultant relatively rapid flow within membrane 26, in combination with the relatively slower flow through prefilter 28 due to its relatively smaller pore size. The sample is forced to flow laterally through diffusing membrane 26 as it contacts receiving surface 24 of prefilter 28. According to another arrangement, diffusing member 26 contains pores oriented substantially parallel to receiving surface 24, that is, the distribution of pore orientation favors lateral capillary flow within the membrane. In this way, rapid lateral diffusion of a sample by diffusing membrane 26 occurs. According to another arrangement, The capillarity of diffusing membrane 26 is greater than the capillarity of prefilter 28, due to a greater depression in fluid sample surface tension within diffusing membrane 26.

In any case, when delivering member 20 is constructed of diffusing membrane 26 and prefilter 28, membrane 26 and prefilter 28 are selected so that, when a sample is applied to diffusing membrane 26, a fluid sample film is rapidly formed on receiving surface 24 of prefilter 28, whereupon the film is allowed to permeate prefilter 28 and to wet test assay surface 10 evenly and equally. As used herein, the term "film" is meant to define a fluid front that is substantially parallel to receiving surface 24 and test assay surface 10. This is to be distinguished from a fluid front which results from application of a fluid sample to a prior art prefilter having no diffusing material at a receiving surface thereof. Fluid applied to such prior art prefilters radiates into the prefilter equally in all directions, that is, the fluid will reach a delivering surface of the prefilter and contact the test assay surface prior to its complete lateral permeation to the edges of the prefilter, and fluid therefore will wet gradually a test assay surface radially from a central location. When such a prior art prefilter is used in association with a test assay surface and detection reagent in accordance with the present invention, uneven distribution of label on test assay surface 10 results. This phenomenon is described more fully below.

Prefilter 28 and diffusing material 26 of the present invention are selected such that delivering member 20 uniformly wets test assay surface 10 substantially instantaneously across its entire surface, due to the formation of a fluid sample film at receiving surface 28 and permeation of that film through the prefilter and to test assay surface 10. This ensures that analytes in the sample are applied in uniform amounts across The test assay surface.

To achieve rapid lateral flow of a fluid sample across receiving surface 24 of prefilter 28, especially when diffusing membrane 26 and prefilter 28 are constructed of the same material, the dimensions of pores in diffusing membrane 26 and the thickness of this membrane can be selected within prescribed ranges relative to the pore dimensions of prefilter 28. Similarly, to achieve adequate filtration while rapidly delivering a sample from receiving surface 24, through prefilter 26 in a direction perpendicular to receiving surface 24 and evenly to test assay surface 10, prefilter 28 can be selected to have a pore size within a prescribed range. Additionally, delivering member 20 is constructed so as to provide rapid and even delivery of a small, undiluted fluid sample to test assay surface 10. These objects may be achieved, for example, by selecting a prefilter 28 having a pore size of from about 0.1 micron to about 1 micron, preferably from about 0.2 micron to about 0.7 micron, more preferably from about 0.33 micron to about 0.53 micron, and a diffusing membrane 26 having a pore size of from about 5 to about 40 microns, preferably from about 8 to about 30 microns, and more preferably from about 10 to about 20 microns. According to a particularly preferred selection of material for fabrication of prefilter 28 and diffusing membrane 26, both are fabricated from a cellulosic membrane material, preferably nitrocellulose, the prefilter 28 having a thickness of from about 50 microns to about 300 microns, more preferably from about 110 microns to about 185 microns, and the diffusing material 26 having a thickness from about 105 to about 165 microns.

If a prefilter of a diameter different from that illustrated and described herein is selected, it may be desirable to construct delivering member 20 such that the amount of diffusing material 26 applied to receiving surface 24 of prefilter 28 is adjusted accordingly. For example, if receiving surface 26 comprises a surfactant, it may be desirable to increase the amount of surfactant applied to receiving surface 24 as the diameter of prefilter 28 is increased. Or, delivering member 20 may be constructed with surfactant arranged nonuniformily on receiving surface 24 of prefilter 28, with more surfactant being applied at the center of the receiving surface and the amount of surfactant decreasing radially across the prefilter.

When a membrane is selected to serve as diffusing material 26, delivering member 20 may be constructed such that a membrane serving as diffusing material 26 decreases in thickness radially, so as to have a greater thickness at the center of prefilter 28 and a lesser thickness at the periphery thereof. Or, when the diameter of prefilter 28 is increased to cover a larger test surface area, it may be desirable to increase the thickness of diffusing membrane 26. Additionally, diffusing material 26 may include a combination of a membrane and a surfactant applied to any portion of the membrane, or applied to the receiving surface 24 of prefilter 28. That is, delivering member 20 may include prefilter 28, a surfactant applied to receiving surface 24 thereof, and a diffusing membrane 26 applied to receiving surface 24 following surfactant application. This may be especially advantageous if a delivering member having a particularly large diameter is constructed. The thickness of prefilter 28 may remain substantially the same over a wide range of diameters, if diffusing material 26 is selected so as to rapidly and evenly distribute a sample across receiving surface 24 of prefilter 28 of large diameter. However, the thickness of prefilter 28 may be adjusted so as to provide greater or lesser sample retention, greater or lesser filtration, or for a variety of reasons.

When delivering member 20 is positioned so as to transfer a sample to test assay surface 10, delivering member 20 is oriented substantially parallel to test assay surface 10, and delivering surface 22 is held in even contact with assay surface 10. Referring to FIG. 1 (in which, for purposes of illustration, delivering surface 22 is not held in even contact with assay surface 10) this is illustrated by application of a sample near the center of diffusing material 26, whereupon the sample is rapidly and evenly diffused laterally, or radially from the center, by diffusing material 26 in the direction of arrows 30, so as to rapidly and evenly spread the sample across the entire receiving surface 24 of prefilter 28. Diffusing material 26 and prefilter 28 are selected such that lateral diffusion is fast enough, relative to any permeation of sample through prefilter 28, that a sample fluid film is formed at receiving surface 24. Prefilter 28 rapidly and evenly transfers the sample, as a film, from receiving surface 24, in a direction substantially perpendicular to the plane of receiving surface 24, to test assay surface 10, while filtering the sample of small particles. As used herein, the term "film" is meant to define a thin layer of sample fluid, having a fluid front that is maintained substantially parallel to test assay surface 10, so that surface 10 is contacted by the sample at all regions thereof substantially instantaneously and with a uniform portion of the sample being applied at any particular region of the surface 10.

Selection of material for use as delivering member 20 can be made in conjunction with selection of fluid as the test assay medium. When the test assay fluid medium is water, cellulosics, and in particular nitrocellulose, is preferred for both prefilter 28 and diffusing member 26. When delivering member 20 is to be used to transfer a biological sample, such as a serum or blood sample, to an assay surface, delivering member 20 (including prefilter 28 and, according to one embodiment, diffusing membrane 26) may advantageously be blocked to prevent binding of sample constituents thereto. Blocking agents useful for achieving this are those agents capable of blocking all binding sites that could hinder solvent transport of sample components or reagents of the invention. Any blocking agent can be selected so as to be inert with respect to any sample components. That is, any agent that would specifically interact with any sample component can be avoided. A suitable blocking agent may comprise a naturally occurring or synthetic, proteinaceous or non-proteinaceous material. A non-limiting exemplary list of material suitable for such a blocking agent includes casein, gelatin, albumins such as bovine serum albumin, bovine gamma globulin, apoferritin, ovalbumin, avidin, peptides, polyamino acids and synthetic polyamino compounds, total serum, non-proteinaceous polyamino acids and synthetic polyamino compounds. Additionally, prefilter 28 and diffusing membrane 26 may be coated with a surfactant, as described above, to achieve blocking.

The size of any sample applied to sample receiving surface 24 of delivering member 20 can be selected in conjunction with the size of delivering member 20 and the retention (void) volume thereof such that the sample volume does not exceed that amount that would adversely effect the desired flow characteristics of delivering member 20. When porous material is selected as solid phase 11, it is desirable to select a sample volume of a size smaller than that which would completely fill the retention volume of delivering member 20 and that of solid phase 11. Preferably, a sample size is selected to permeate delivering member 20, and to wet test assay surface 10 of test assay solid phase 11 only to the extent necessary to perform the test assay. For example, if all immobilized test assay reagents at test assay surface 10 reside substantially at the surface, rather than within test assay solid phase 11, it is desirable that the fluid sample does not permeate into test assay solid phase 11 to a significant extent. On the other hand, if test assay reagents are immobilized within assay solid phase 11, that is, below surface 10, it would be desirable for a fluid sample to permeate into test assay solid phase 11 to the extent necessary to contact the immobilized reagents. Additionally, it is desirable for a test assay fluid to wet test assay surface 10 to the extent that a desired degree of non-specific binding of a later-applied labeled reagent occurs. This is described more fully below.

Additionally, it is desirable to select a sample volume of a size facilitating permeation of delivering member 20 via capillarity as opposed to gravity. A preferred sample volume is that which rapidly and evenly forms a film across receiving surface 24 with the aid of diffusing material 26, and which then rapidly and evenly permeates prefilter 28 by capillary action, and which evenly wets test assay surface 10 at all portions thereof substantially instantaneously. The amount of any sample that would adversely effect such flow characteristics would be somewhat dependent upon the amount of particulate matter in the sample. When a blood sample is used, this would depend upon the treatment of the blood sample. If the sample were treated so as to remove most particulate matter prior to application of the sample to receiving surface 24, a larger volume of sample could be used. Generally, a preferred sample volume is from about 1 to about 3 times the retention volume of delivering member 20, preferably from about 1 to about 2 times the retention volume of member 20, more preferably from about 1.1 to about 1.4 times the retention volume of member 20.

Delivering member 20 is particularly useful in immunoassay procedures, but is not limited to them. It may find use in a wide variety of procedures in which a fluid sample is desirably rapidly and evenly transferred to any surface, which sample may optionally be filtered as well. The fluid sample generally contains an analyte, including a wide variety of species including drugs, hormones, macromolecules, microorganisms (all of which may be found in clinical or physiological fluids such as cerebral spinal fluid, ocular lens liquid, whole blood, blood serum, plasma, saliva, tears, urine), synthetic chemicals, pollutants in water and air, trace compounds, toxins and microorganisms in food, and dilutions thereof. The fluid carrier may be aqueous or organic, and selection of material for use in fabrication of member 20 can be made based in large part on the fluid carrier. Samples may be analyzed to determine the presence and/or concentration of a wide variety of analytes such as those described in U.S. Pat. No. 4,366,241, issued Dec. 28, 1982 to Tom et al., referenced above.

Test assay solid phase 11, and in particular surface 10 thereof, can be selected such that a test assay reagent may be conveniently immobilized thereon. Surface 10 may include one, or a plurality of specific areas at which one or more test assay reagents are immobilized. Typically, an immobilized assay reagent is selected as one member of a binding partner pair.

immobilization of a member of a binding partner pair onto test assay surface 10 may be achieved via covalent or absorptive attachment. According to one embodiment, test assay surface 10 includes exposed functional groups including, but not limited to, carboxyl groups, sulphonic acid groups, amino groups, thio groups, hydroxyl groups, pyridyl groups, phosphoryl groups, derivatives of any of these, or other functional groups known to those of ordinary skill in the art that would facilitate immobilization. These functional groups can also be present in an activated form, activated by the introduction of a substituent such as, for example, halogen, phenyl, carboxyl or sulphonyl or the like. Test assay solid phase 11 may be formed with an analyte binding partner immobilized therein or thereon as a result of the formation process, as described in U.S. Pat. No. 4,098,645, issued Jul. 4, 1978, and incorporated herein by reference. Additionally, plasma immobilization of proteins on polymeric matrices are described in U.S. Pat. No. 5,028,657, issued Jul. 2, 1991 and incorporated herein by reference, and such immobilization is within the scope of the present invention. DNA, RNA and certain antigens may be immobilized against solvent transport by baking onto the test assay surface 10. Generally, when test assay surface 10 comprises nitrocellulose or a mixed nitrocellulose ester, no special chemical linkage is required for the immobilization of assay reagents thereon. That is, immobilization may be absorptive.

As illustrated in FIG. 1, surface 10 includes first area 12 having a first assay reagent 14 immobilized thereon (Protein A is illustrated) and a second area 16 carrying a second immobilized assay reagent 18 (HIV is illustrated). Any number of areas carrying immobilized assay reagents may be provided on test assay surface 10, and these reagents may serve as analyte binding partners, control binding partners, or a combination. Test assay surface 10 of test assay solid phase 11 may be blocked according to the invention, but need not be.

As noted, according to one embodiment test assay solid phase 11 is porous, and may be fabricated from any of the materials described above which are suitable for use in fabrication of prefilter 28. According to this embodiment, and especially when test assay solid phase 11 and prefilter 28 are fabricated from the same material, solid phase 11 has a pore size as large as or larger than that of prefitter 28. Also, solid phase 11 can have a pore size selected to facilitate rapid flow of sample, and detection reagent (described more fully below), so as to minimize non-specific binding at test assay surface 10. Specifically, solid phase 11 can have a pore size of from 1 to 100 microns, preferably from about 5 to 40 microns, more preferably from about 8 to about 30 microns, and most preferably from about 10 to about 20 microns.

The size and shape of delivering member 20 and test assay solid phase 11 may take a variety of forms and values. For example, delivering member 20 and test assay solid phase 11 need not be the same size or shape. Only a portion of the exposed surface of solid phase 11 as illustrated may define test assay surface 10, or the entire exposed surface may define the test assay surface. Additionally, delivering surface 22 of member 20 may be defined by only a portion, or all, of an exposed surface of member 20. It is important only that any portion of delivering member 20 defining delivering surface 22 is brought into even contact with the entire exposed surface of solid phase 11 that defines test assay surface 10.

According to the embodiment illustrated, delivering member 20 and test assay solid phase 11 are both substantially circular, and each has a diameter of approximately 1.5 centimeter. The thickness of test assay solid phase 11 is not critical to the present invention, but if a porous solid phase 11 is selected, it is advantageous to select one with a retention volume equal to or greater than the difference between the volume of sample applied to delivering member 20 and its retention volume. In this way, solid phase 11 adds to the rapid an even transfer of a fluid sample from receiving surface 24 onto assay surface 10.

Referring now to FIG. 2, an exemplary test assay is illustrated, utilizing a test assay kit in accordance with the present invention. In all of the figures, each component common to several of the figures is given a single numerical designation. The kit includes (FIG. 2a) delivering member 20, and utilizes a detection reagent described more fully in co-pending Application entitled "Assay Employing Both Protein and Antibody", by Dorval et al., referenced above. Specifically, a highly-sensitive HIV detection analysis according to the present invention is illustrated. With reference to FIG. 2, the assay includes Protein A as a first immobilized assay reagent 14 and HIV as a second immobilized assay reagent 18 on first area 12 and second area 16, respectively, of test assay surface 10.

In FIG. 2, delivering member 20 is represented schematically, and diffusing material 26 is not shown. Therefore, receiving surface 24 of prefilter 28 (not shown) is represented as a receiving surface of delivering member 20 as a whole. Delivering member 20 is placed upon test assay solid phase 11 such that delivering surface 22 evenly contacts test assay surface 10. Sample is added to sample receiving surface 24 of delivering member 20 (FIGS. 2b, 2e), preferably substantially in the center of surface 24, whereupon the sample is rapidly radially diffused by diffusing material 26 (not specifically illustrated) so as to form a film, and the film is evenly transferred to test assay surface 10, so as to contact all portions of surface 10 substantially simultaneously. Delivering member 20 includes a prefilter (not specifically illustrated) which filters the sample of particulate material 32 of a dimension larger than the smallest pore dimension of the prefilter.

Figure 2A:
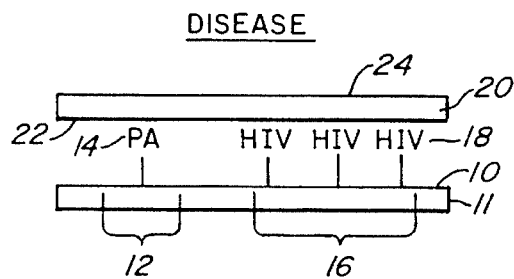
FIGS. 2a–2f schematically illustrate a test assay procedure for the determination of both IgG and one of IgA, IgM, or a combination in a single sample according to one embodiment of the invention, using an assay kit according to one embodiment of the invention.
Figure 2D:
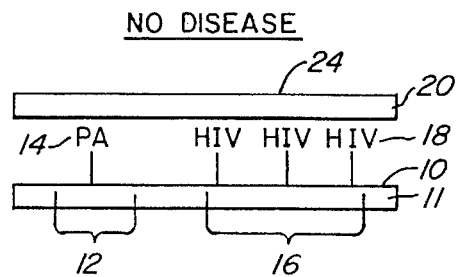
Figure 2B:
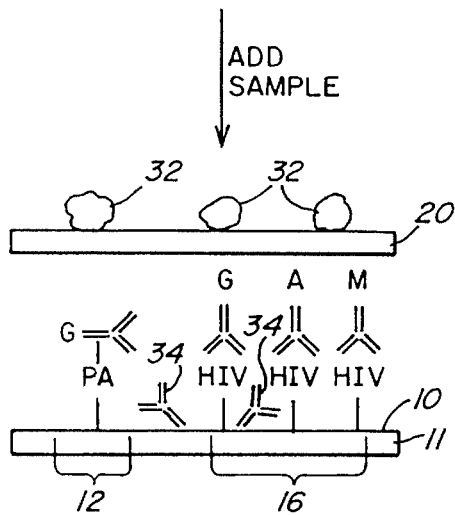
Figure 2E:
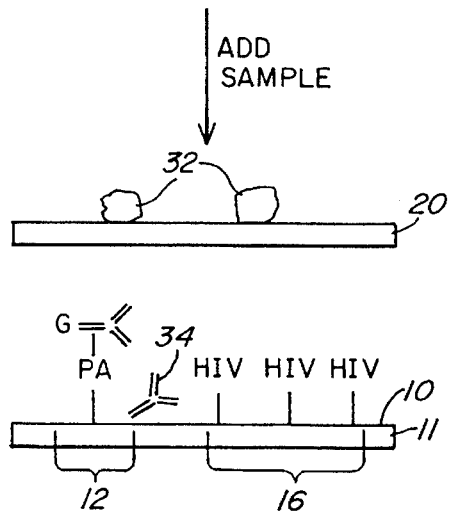

After a sample has been delivered to assay surface 11 via delivering member 20, any binding partners of first or second immobilized assay reagents 14 and 18 will bind thereto. As illustrated (FIG. 2a), a sample containing all of IgG, IgA and IgM specific for HIV are captured by HIV immobilized at second immobilized assay reagent area 16. IgG has also been captured at first immobilized assay reagent area 12 by immobilized Protein A, and this serves as a control as IgG is present in large amounts in all serum samples. If no disease is present, that is, if no antibodies to HIV are present in The sample, species in the sample will not bind to the immobilized HIV at area 16 (FIG. 2e). Inevitably, some sample components will remain at test assay surface 10, unbound to any immobilized assay reagents, and this is indicated at 34.

Figure 2C:
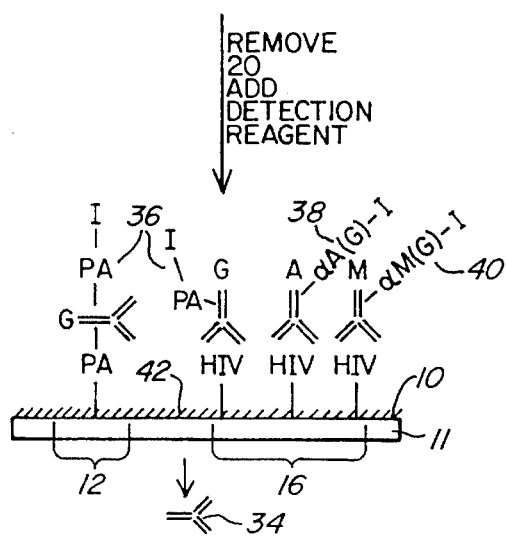
Figure 2F:
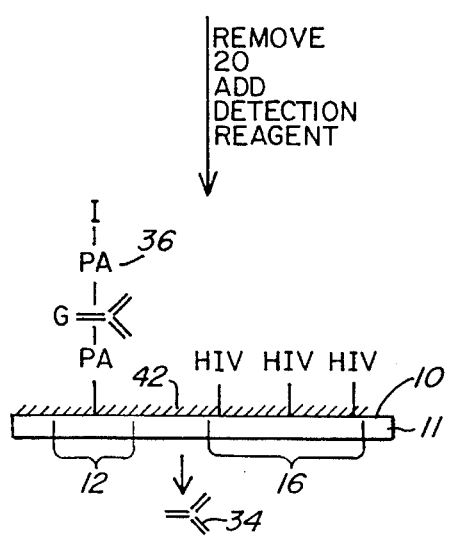

Subsequently, delivering member 20 is removed and an excess of a detection reagent is deposited upon test assay surface 10 (FIGS. 2e, 2f). According to the assay illustrated, the detection reagent includes Protein A 36 coupled to a hydrophobic label, specifically indigo, which binds to IgG bound to Protein A at area 12 of surface 10, and to IgG bound to HIV at area 16 of surface 10. The reagent also includes anti-IgA-IgG 38 which binds to IgA bound to HIV at area 16 of surface 10, and anti-IgM-IgG 40 which binds to IgM bound to HIV at area 16 of surface 10. Indigo is hydrophobically coupled to each of anti-IgA-IgG 38 and anti-IgM-IgG serving both as a label and a blocking agent blocking the binding site on each from interaction with Protein A 36.

As noted above, the pore dimension of test assay solid phase 11 is most preferably from about 10 to about 20 microns. The relatively large pore size of test assay solid phase 11 and the resultant rapid rate of flow of the excess detection reagent through the solid phase 11 results in a reduction in non-specific binding as extraneous species 34 is swept through solid phase 11 from test assay surface 10, and eliminates the need for a wash step between the step of applying sample and the step of applying detection reagent. Additionally, the rapidity of application of sample to assay surface 10, followed by rapid introduction of detection reagent, allows insufficient time for significant non-specific binding to be established.

After the addition of the detection reagent, the presence of label, specifically indigo detected visually without the aid of a microscope, at both first immobilized assay reagent area 12 and second immobilized assay reagent area 16 is indicative of a sample containing antibodies to HIV. The presence of label at first immobilized assay reagent area 12 only (i.e. label at area 16) indicates the absence of antibodies to HIV.

An aspect of the assay is the ability to detect the evenness of the distribution of the sample across the test assay surface. Assay reagents are immobilized at areas 12 and 16, and optionally additional areas (not shown), and other areas of surface 10 remain free of reagent immobilization. Surface 10 is selected so that the areas remaining free of immobilized assay reagent expose a chemical functionality that allows non-specific binding of labeled reagent to one degree when surface 10 is first addressed by a sample to a first extent, and to a different degree when surface 10 is first addressed by a sample to a second extent. In other words, even after sample is applied, a low level of non-specific binding of labeled reagent to surface 10 occurs. If the sample is applied to surface 10 unevenly, then those regions with less sample applied will bind more label non-specifically. Thus, an even tint across the surface 10 indicates an even distribution of sample, whereas uneven tint indicates uneven distribution. According to the invention, if no sample is applied to any particular region, then non-specific binding of the label will be very strong and the surface 10 will have dark blotches on it. Preferably, however, the sample acts to only partially block non-specific binding of label to provide not only an absolute, but also a relative measure of sample distribution. Therefore, the evenness of distribution of excess indigo 42 across test assay surface 10 is an indication of the evenness of the preceding distribution of the serum sample on surface 10 by delivering member 20, as the serum sample serves to block surface 10 during the assay. Thus, this may serve an indication of the reliability of the particular test.

Figure 3A:
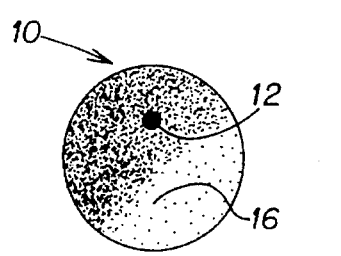
FIGS. 3(a–c) illustrate the appearance of a test assay surface according to one embodiment of the present invention after a test assay as illustrated in FIG. 2 has been performed in which the result is error, negative, and positive, respectively.
Figure 3B:
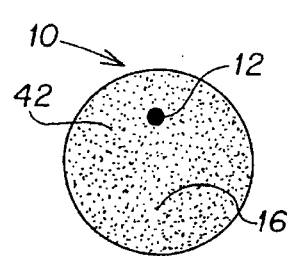
Figure 3C:
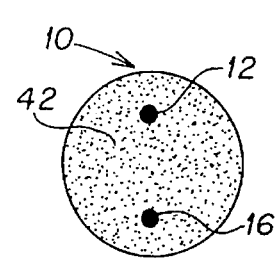

Referring now to FIGS. 3a–c, the appearance of test assay surface 10 after the assay illustrated in FIG. 2 has been performed and indicating error (a), a negative test (b), and a positive test (c), is illustrated. FIG. 3a indicates error as dye has been unevenly non-specifically bound to test assay surface 10, indicating that serum has been unevenly applied to surface 10. Another indicator of a test error (not illustrated) is a completely dark test assay surface 10, indicating dye completely coating surface 10. This may be the case if serum does not adequately coat surface 10 prior to the addition of the detection reagent. Referring now to FIG. 3b, the presence of dye at area 12 and the presence of lightly shaded dye background across surface 10, and the absence of dye at area 16 signifies absence of infection. IgG has bound to Protein A immobilized at area 12 which has in turn been coupled to dye-coupled Protein A in the detection reagent. However, no antibody to HIV has been immobilized at area 16, indicated by the lack of labeled detection reagent immobilized at area 16. Referring to FIG. 3c, infection is indicated as labeled components in the detection reagent are bound at both areas 12 and 16, signifying the presence of antibodies to HIV in the serum sample bound to immobilized HIV at area 16. In all cases label bound at area 12 serves as a control according to the assay illustrated.

Figure 4:
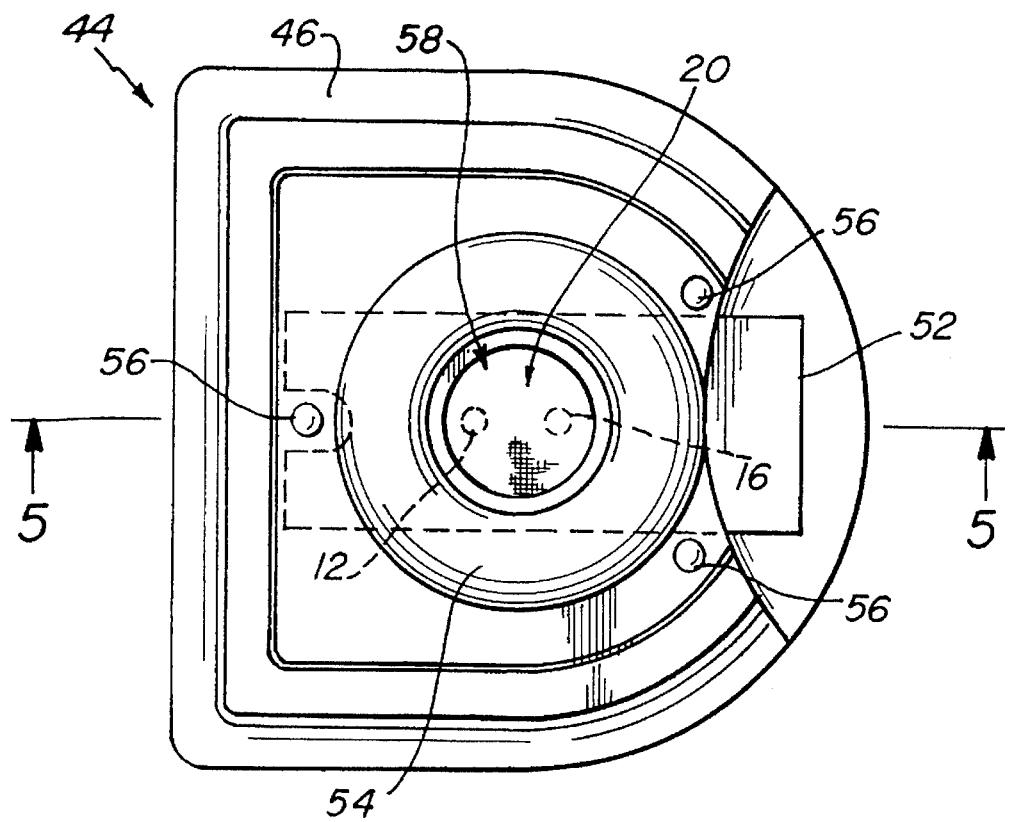
FIG. 4 is a top view of a test assay kit according to one embodiment of the present invention.
Figure 5:
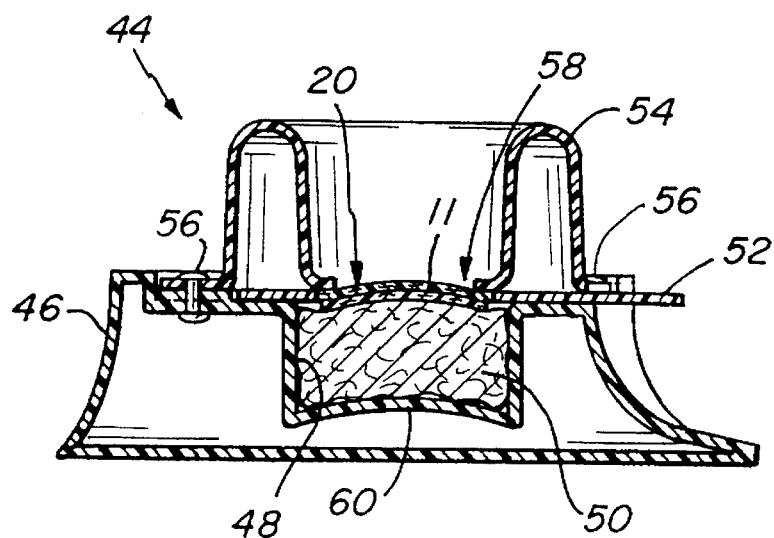
FIG. 5 is a cross-section through lines 5—5 of FIG. 4.

Referring to now FIGS. 4 and 5, an exemplary assay kit arrangement in accordance with the present invention is illustrated generally at 44 and includes base 46 having cavity 48 formed therein. Cavity 48 has a dome 60 protruding upward from its bottom surface. Cavity 48 houses a resilient, absorbent member 50, such as a cotton ball, which is arranged to protrude above the top of base 46 when naturally expanded. Resilient, absorbent member 50 supports test assay solid phase 11 at the top of cavity 48, that is, even with the top of base 46, when a force is directed downwardly against the expansive force of member 50, as described below. Sample delivering member 20 is mounted within and is integral with rectangular tab 52 which extends across a portion of base 46, and across cavity 48 so as to place delivering member 20 directly above test assay solid phase 11. When membranes define both prefilter 24 and diffusing member 26 (not illustrated in FIGS. 4 and 5), tab 52 acts as a connector connected to the periphery of prefilter 24 and the periphery of diffusing membrane 26, and holding the receiving surface of prefilter 24 in face to face relation with diffusing membrane 26. Tab 52 and delivering member 20 are held in place by a cover 54 which may be attached to base 46 by way of rivets or snaps 56, by sonication welding, or the like. Cover 54 includes an opening 58 which exposes most of delivering member 20, and the periphery of which resists an upward force provided by absorbent member 50 onto delivering member 20 via test assay solid phase 11. In this way, delivering surface 22 of delivering member 20 is held in even contact with test assay surface 10 of test assay solid phase 11. If a membrane defines diffusing member 26, diffusing membrane 26 and receiving surface 24 of prefilter 28 are held in even contact in this manner as well. A downward force on the periphery of diffusing material 26 of delivering member 20 is supplied by the periphery of opening 58 of cover 54, and an upward force on test assay solid phase 11 is supplied by resilient absorbent member 50, acting as an urging member. Tab 52 extends out from under cover 54 so that delivering member 20 can be quickly and easily removed from under cover 54 and from test assay solid phase 11.

When a sample is applied to delivering member 20 at receiving surface 24 (prefilter 28 is not shown), it is filtered, and is rapidly and evenly delivered by member 20 to test assay surface 10. This may be observed during the assay by the radial wetting of the visible receiving surface 24 (or the top surface of diffusing membrane 26). When surface 24 is completely wet, a few seconds are allowed for the fluid sample film to completely permeate prefilter 28 and to wet test assay surface 10. Then, tab 52 may be removed from under cover 54. Absorbent, resilient member 50 then urges test assay solid phase 11 upward against the periphery of opening 58 of cover 54. Cover 54 is constructed so as to provide a fluid well about opening 58. A detection reagent may then be introduced into the fluid well, which detection reagent rapidly flows through test assay solid phase 11 and is absorbed by absorbent, resilient member 50. Test assay surface 10 will then give a visual indication as to a positive or negative test result, or an error, as illustrated in FIGS. 3(*a–c*). The entire process takes less than 1 minute, typically about 30 seconds.

If tab 52 completely covers the cavity 48 formed in base 46, a hole may be formed in the cavity so as to allow air displaced by fluid absorbed by absorbent member 50 to escape. If tab 52 does not completely cover cavity 48, no hole is needed as air will escape around tab 52.

As illustrated, test assay solid phase and delivering member form a slight dome due to the upward force of resilient, absorbent member 50. This arrangement is understood to be consistent with the description of components of the test assay kit of the present invention, as described above, in which it is desirable that delivering member, and in particular delivering surface 24 of prefilter 28, and test assay surface 10, are arranged substantially parallel to each other. Additionally, the above-described radial diffusion of test assay fluid by diffusing material 26 in a manner substantially parallel to delivering surface 24 is to be understood to include diffusion across the slightly dome-shaped delivering member 20 as illustrated in FIG. 5.

The following examples are intended to illustrate the benefits of the present invention, but do not exemplify the full scope of the invention. For example, although dyes and pigments are exclusively exemplified as labels, a variety of labels may be employed. Although nitrocellulose as delivering member and test assay surface material is exclusively exemplified, a variety of porous materials would be suitable in fabrication of these components. As a substantially circular test assay surface and delivering member are exemplified, a variety of shapes and sizes of these features may exist. While immobilization of antigen to detect antibodies specific for the immobilized antigen in a serum sample, with immobilization of protein to capture IgG as a control is exclusively exemplified, any of a variety of test assays may be carried out. The above-described and other modifications and their equivalents are understood to be within the scope of the present invention.

EXAMPLE 1

PROCEDURE FOR PRODUCING FROZEN STOCKS OF HIV1

In this and the following examples, all chemicals were obtained from Sigma Chemical Corporation (St. Louis, Mo.) unless otherwise noted.

Preparation of required solutions:

An LB solution was prepared by dissolving 5 grams of yeast extract (DIFCO/VWR), 10 grams of tryprone (DIFCO/VWR), and 10 grams of NaCl in 1 liter of MilliQ water, adjusting the pH to 7.2, and sterilizing by autoclaving. MilliQ water was obtained by filtration of water through a MilliQ water system (Millipore Corp., Bedford, Mass.). The solution was allowed to cool and Ampicillin was added to bring the final concentration to 0.1 mg/ml.

SOB Broth was prepared by dissolving 5 grams of yeast extract and 20 grams of tryprone in 1 liter of MilliQ Water containing 10 ml of a 1M NaCl stock, and the pH was adjusted to 7.5. The solution was autoclaved and allowed to cool. The final solution was adjusted to 20 mM $MgCl_2$/$MgSO_4$, by the addition of 10 ml of a 1M $MgCl_2$ stock and 10 ml of a 1M $MgSO_4$ stock.

FSB solution was prepared as described in Maniatis (Molecular Cloning), §1.78. The following components were added to MilliQ water: 10 ml of 1M potassium acetate (pH 7.5), 8.91 g of $MnCl_2.4H_2O$, 1.47 g of $CaCl_2.2H_2O$, 7.46 g of KCl, 0.80 g of hexaminecobalt chloride, and 100 ml of glycerol (Amresco). The solution was adjusted to 1 liter with MilliQ water and the pH adjusted to 6.4 with 0.1N HCl (J. T. Baker, Phillipsburg, N.J.).

Preparation of *E. Coli* HIV1 stocks:

LB Broth (10 ml) was innoculated with 0.2 ml of a glycerol (Amresco) stock and then grown overnight in an incubator shaker at 28° C. and 300 RPM. The overnight culture was added to 200 ml SOB containing 20 mM MgCl$_2$/MgSO$_4$ in a 1 Liter Pyrex Fernbach Flask and the mixture was grown until the optical density was 0.6 to 0.7. The cells were then transferred to sterile, disposable, ice-cold 50 ml polypropylene tubes (Falcon) and the cultures cooled to 0° C. by storing the tubes on ice for 10 minutes. The remaining steps were carried out aseptically.

The cells were recovered by centrifugation at 4000 rpm for 10 minutes at 4° C., using a TZ-28 rotor (Sorvall) in a RC-5B centrifuge (Sorvall). After the supernatant was completely removed and discarded, the pellet was resuspended by gentle vortexing, in approximately 80 ml (20 ml per 50 ml tube) of ice-cold FSB. The cells were allowed to stand on ice for 10 minutes and were recovered by centrifugation at 4000 rpm for 10 minutes at 4° C. After the supernatant was completely removed and discarded, the pellet was resuspended by gentle vortexing in approximately 20 ml (5 ml per 50 ml tube) of ice-cold FSB. 0.7 ml (175 ul per 50 ml tube) of DMSO was gently mixed into the solution and the suspension was returned to an ice bath. An additional 175 ul (per 50 ml tube) of DMSO was added to the suspensions, mixed gently and then returned to an ice bath. The suspensions were aliquoted (0.2 mls) into chilled, sterile microfuge tubes and then frozen by immersion of the tightly closed tubes in a methanol dry ice bath. The tubes were stored at −80° C. until needed.

Production of HIV1 from a frozen DMSO stock:

At least two days after freezing the cells, the high yield induction of HIV1 from a starter culture, which was grown from a frozen DMSO stock, may be determined in order to perform this analysis the stock was removed from an −80° C. freezer and thawed on ice. 0.2 ml of cells were added to 1 ml of SOB medium, and then incubated for 1 hour at 28° C. The starter culture was prepared by adding this 1.2 ml culture to 200 ml LB medium (0.1 mg/ml Ampicillin (Amresco)) and incubating at 28° C. overnight. The HIV1 was then purified as described in Example 2.

EXAMPLE 2

PROCEDURE FOR PRODUCING AND PURIFYING HIV 1

Preparation of required solutions:

LB Broth was prepared by dissolving 17 grams of yeast extract (DIFCO/VWR), 34 grams of tryprone (DIFCO/VWR), and 34 grams of NaCl in 3.4 liters of MilliQ water (Millipore Corp.), adjusting the pH to 7.2, and sterilizing by autoclaving. The solution was allowed to cool and Ampicillin (Amresco) was added to a final concentration of 0.1 mg/ml.

One Liter of 50 mM Tris-HCl, 2 mM EDTA, pH8.0 was prepared as follows: 6 grams of TRIZMA BASE and 744 milligrams of EDTA were dissolved in MilliQ water (Millipore Corp.), the pH was adjusted to 8.0 with HCl (J. T. Baker), and the final volume of the solution was adjusted to 1 liter with MilliQ water.

In order to prepare one liter of Extract Buffer 480.5 grams of LrREA (8M) (Amresco), 4.08 grams of BICINE (25 mM), 1.54 grams of DTT (10 mM), and 1.86 grams of EDTA (5 mM) were dissolved in MilliQ water containing 1 ml of TWEEN 20 (0.1%, polyoxyethylene sorbitan monolaurate, Calbiochem, La Jolla, Calif.). The pH of the solution was brought to 8.5, and the volume was adjusted to one liter with MilliQ Water.

One liter of 25% Ammonium Sulfate was prepared by dissolving 250 grams of ammonium sulfate in one liter of MilliQ water.

Growth of and induction of 3 liters of *E. coli* containing HIV1:

The culture from Example 1 was innoculated into a 1 Liter Pyrex Fernbach Flask containing 200 ml LB Broth, and grown overnight in an incubator shaker at 25° C. and 300 RPM. 10 ml of this culture was saved and stored at 4° C. for an experimental control (UNINDUCED CONTROL). The next day 50 ml of the culture was used to innolculate 3×2.8 Liter Pyrex Fernbach Flasks each containing 1 liter LB Broth. The cultures were grown in the incubator shaker at 30° C. and 300 RPM until the OD was 0.6–1.0 at 600 nm (2 to 3 hours).

The cultures were removed from the 30° C. incubator shaker and a 160–170 ml aliquot was transferred into a sterile 0.5 Liter Pyrex Fernbach Flask. The temperature of the culture aliquot was quickly raised by transferring the 0.5 liter flask into a 60°–70° C. water bath. While it was immersed in the water bath the flask was shaken and the temperature of the culture inside was monitored. As soon as the culture reached 42° C. (after 2 to 3 minutes), the contents of the flask was transferred into a preheated 2.8 Liter Pyrex Fernbach Flask (6 empty, sterile 2.8 Liter Pyrex Fernbach Flasks were preheated in a shaker at 42° C. and 200 RPM). This procedure was repeated until each of the 6 flasks contained 0.5 liters of induced culture. The flasks were covered and the shaker speed was raised to 400 RPM. A 1 ml aliquot was removed from each of the 6 flasks and saved as an experimental control for induction (INDUCED CONTROL). The cultures were incubated at 42° C. and 400 RPM overnight. The next day the cells were harvested by centrifugation in a rotor (Sorvall) in a Sorvall RC-5B centrifuge at 8000 RPM for 20 minutes. If the cells were not required for immediate purification, they were stored at −80° C.

Extraction and purification of inclusion bodies:

The cell pellet was thawed and resuspended in a total of 300 ml of 50 mM Tris-HCl pH 8.0, 2 mM EDTA (100 ml/1 L culture ratio). In order to enable efficient resuspension, the solution was sonicated (Branson sonifier Model 450) and lysozyme was added to a final concentration of 100 mg/ml (3 ml of a 10 mg/ml stock freshly prepared in 50 mM Tris-HCl pH 8.0, 2 mM EDTA was used). 1/100 of a volume of 10% Triton X-100 (3 ml) was added, and the solution was incubated at 30° C. for 15 minutes. The solution was then cenrifuged in a Sorvall RC-5B at 8000 RPM in a GS-3 rotor for 1 hour. If the supernatant was not clear the centrifugation was continued for another hour or the solution was spun at 15000 RPM in a TZ-28 rotor. The supernatant was collected and stored at 4° C. until an aliquot (100 uls) had been analyzed by Polyacrylimide Gel Electrophoresis (PAGE) (LYSOZYME SUP). The pellet was resuspended with sonication in a total of 300 ml of 50 mM Tris-HCl pH 8.0, 2 mM EDTA (100 ml/1 L culture ratio) and 100 ul was removed (LYSOZYME PREC) for PAGE analysis. Centrifugation was performed as described above (in a Sorvall RC-5B at 8000 RPM in a GS-3 rotor (Sorvall) for 1 hour) and 100 ul of the supernatant was removed for PAGE analysis (WASH SUP). The pellet was resuspended with sonication in a total of 60 ml of Extract Buffer (20 ml/1 L culture ratio). A 20 ul aliquot was saved for an experimental control (EXTRACT 1). The cell suspension was then centrifuged in a Sorvall RC-5B at 15000 RPM in a TZ-28 rotor for 30 minutes. The supernatant was transferred to a fresh tube for further purification (SOLUTION 1). The pellet was resuspended in 30 ml of Extract Buffer and centrifuged as described in the previous step (15000 RPM in a TZ-28 rotor for 30 minutes). Before centrifugation a 20 ml aliquot was removed for an experimental control (EXTRACT 2). The supernatant was transferred to a fresh tube for further purification (SOLUTION 2). 20 ml aliquots of SOLUTION 1 and SOLUTION 2 were removed for an experimental control.

SOLUTION 1 and 2 were combined and the inclusion bodies were precipitated by adding 5 volumes of 25% Ammonium Sulfate (450 ml). The solution was centrifuged in a Sorvall RC-5B at 8000 RPM using a GS-3 rotor (Sorvall) for 1 hour. If the supernatant was not clear the centrifugation was continued for another hour or the solution was centrifuged at 15000 RPM in a TZ-28 rotor. A 20 ul aliquot of the supernatant was removed for use as an experimental control (SOLUTION 3). The pellet was resolubilized by the addition of 60 ml of Extract Buffer with sonication. A 20 ul aliquot of the resuspended pellet was removed for an experimental control (EXTRACT 3). The solution was precipitated with 300 ml (5 volumes) of 25% Ammonium Sulfate and centrifuged as described above (at 8000 RPM in a GS-3 rotor (Sorvall) for 1 hour). A 20 ul aliquot of the supernatant was removed for use as an experimental control (SOLUTION 4). The pellet was resuspended with sonication in 100 ml (1/30 of the original culture volume) of Extract Buffer (INCLUSION BODIES).

Purification of HIV1 by electroelution:

13 ml Glycerol (Amresco) and 13 ml of 10% SDS (GIBCO BRL, Helgerman, Conn.) were added to the suspension of inclusion bodies (100 ml) obtained in the previous step and aliquots of 16–17 ml were removed for electrophoresis. The remainder of the samples were stored at 4° C. (or at −80° C. for long-term storage).

Preparative SDS Polyacrylamide Gels (37 mm ID) were prepared as described in the BIO-RAD Model 491 Prep Cell Instruction Manual (pages 13–15). 80 ml (10 cm) of a 12% Separating Gel solution and 28 ml (3.5 cm) of Stacking Gel solution were used to pour the gels. The Model 491 Prep Cell (BIO_RAD) was assembled and operated according to the Instruction Manual (pages 15–20). Prior to loading, 50 ul of sample buffer containing Bromophenol Blue and 160 ul of b-Mercaptoethanol were added to each 16–17 ml aliquot of sample. The sample was heated to 90° C. for 10 minutes (this was done by transferring small aliquots of the sample into eppendorf tubes and placing them into a heat block). A total of 16—17 ml of sample was loaded onto each preparative gel. After loading, the Model 491 Prep Cells was operated under a constant current of 40 mA, for 22 h, with an elution buffer flow rate of 30 ml/h (0.5 ml/min), and fractions were collected for 20 min.

10 ul aliquots of sample were collected after the elution of the Bromophenol Blue. These aliquots were run on a 12% SDS (GIBCO/BRL) polyacrylamide gel in order to determine which of them contained the 27.3 kd HIV1 protein. The fractions containing HIV1 were then pooled and further purified by precipitation and resuspension as described below.

The experimental controls were processed as described for each control and 10 ul aliquots of each sample were run on 12% SDS (GIBCO/BRL) polyacrylimide gels under reducing conditions.

INDUCED AND UNINDUCED CONTROLS: Each sample was transferred to an eppendorf tube and spun to separate out insoluble material. The supernatant was discarded and the pellet was resuspended in 0.1 ml MilliQ water.

LYSOZYME SUP, LYSOZYME PREC, SOLUTION 1,2,3 & 4 and EXTRACTS 1, 2 & 3: These controls were diluted with 80 ul of water and run in 10 ul aliquots on PAGE gels.

Precipitation and resuspension of HIV1 for test assay surface blotting:

The pooled HIV1 fractions from electroelution were added to a new centrifuge tube (50 ml, Sarstedt, Newton, N.C.; 250 ml, Corning, Corning, N.Y., or equivalent) which is capable of holding three times the starting volume. Two volumes of 100% ethanol were added to the fraction and mixed well. After incubation for at least 30 minutes at room temperature, the suspension was centrifuged in a Sorvall RC-5, SS34 rotor (Sorvall) at 4000 rpm for 30 minutes, with no brake. The supernatant was decanted and saved, and the tube was inverted to blot off all fluid. The pellet was white, waxy and shiny with a very smooth texture (i.e. not granular). The pellet was resuspended in the smallest amount of 0.1N NaOH possible. To do this, the NaOH must be added in 200 ul increments until there are no visible solids remaining. The solution was then centrifuged in a microfuge for 5 minutes to remove any remaining solids. The protein concentration of this solution was determined and then 5 ug/lane of sample were run on a 15% SDS-PAGE reduced and non-reduced. 0.5 ul containing 2 ug of HIV1 was then be blotted as described in Example 4.

EXAMPLE 3

PREPARATION OF AMYLOSE COLUMN AND ELUTE BUFFER AND PROCEDURE FOR PRODUCING AND PURIFYING HIV 2

Preparation of required solutions:

Amylose column buffer was prepared by dissolving 1.2 grams of trizma base, 11.7 grams of NaCl, and 372 milligrams of EDTA in 900 ml of MilliQ water. Once the chemicals were completely dissolved 700 ul of b-mercapatoethanol was added and pH was adjusted to 7.4 (within 0.1) with 10N HCl. Sterilization was accomplished by filtration of the solution through a 0.45 mm filter unit (Costar, Cambridge, Mass.). The sterile solution was stored at 4° C. This solution should not be used if stored for longer than 30 days.

Amylose elute buffer was prepared by dissolving 1.2 g of Trizma base, 11.7 g of NaCl, 372 mg of EDTA, and 3.42 g of Maltose in 900 ml of MilliQ water. Once the chemicals were completely dissolved 700 ul of b-mercapatoethanol was added and the pH of the solution was adjusted to 7.4 (within 0.1) with 10N HCl (J. T. Baker). The solution was sterile filtered through a 0.45 mm filter unit and stored at 4° C. This solution should not be used if stored for longer than 30 days.

LB Broth was prepared by dissolving 5 grams of yeast extract (DIFCO/VWR), 10 grams of tryprone (DIFCO/VWR), and 10 grams of NaCl in 1 liter of MilliQ water, adjusting the pH to 7.2, and sterilizing by autoclaving. The solution was allowed to cool and Ampicillin (Amresco) was added to a final concentration of 0.1 mg/ml. One liter of LB broth was aliquoted into each of 6, 2.8 Liter Pyrex Fernbach Flasks and 400 ml of LB Broth was aliquoted into a 1 Liter Pyrex Fernbach Flask.

100 ml of 100 mM isopropylthio-b-D-galactoside (IPTG)

500 ml of 20% Ethanol (V/V)

8 Liters of 1× Phosphate Buffered Saline (PBS) pH 7.2

Growth of 6 liters of *E. coli*/MBP construct:

A 1 Liter Pyrex Fernbach Flask containing 400 ml LB Broth (100 mg/ml Ampicillin, Amresco) was innoculated with the transfected culture and grown overnight in the incubator shaker at 37° C. and 250 RPM. 10 ml of this culture was saved at 4° C. for an experimental control (UNINDUCED) Each of 6, 2.8 Liter Pyrex Fernbach Flasks containing 1 liter of LB Broth were innoculated with 50 ml of culture grown in the previous step. Cultures were grown in the incubator shaker at 37° C. and 250 RPM until the O.D. at 600 nm was between 0.6 and 1.0 (2 to 2.5 hours). 3 ml of culture were removed for SDS-PAGE analysis of induction (UNINDUCED 2).

The cultures were induced by adding 10 ml of 100 mM IPTG to each flask. The flasks were covered and incubated for 3 hours at 37° C. and 250 RPM. The final O.D. was measured and an aliquot of 3 ml of culture was removed for SDS-PAGE analysis of induction (INDUCED). The cells were harvested by centrifugation in the Sorvall RC-5B at 8000 RPM for 20 minutes. If cells were not required for immediate purification, they were stored at −80° C.

Induction was analyzed by electrophoresis of the control samples isolated in the above steps. 1 ml of the UNINDUCED, UNINDUCED 2, and INDUCED samples were spun in a microcentrifuge and the pellets were resuspended in 100 ul of MilliQ water. 10 ul aliquots of these cell suspensions are run on a 15% SDS-PAGE gel under reducing conditions.

Extraction of inclusion bodies:

The cell pellet was thawed and resuspend in Amylose Column Buffer at a ratio of 10 ml per every gram of pellet. The samples were sonicated until total suspension was achieved. The suspension was kept chilled by storage in an ice bath during sonication. Once totally suspended, the samples were incubated at room temperature on a tumbler or rocking platform for 4 hours (or overnight). However, one ml of the suspension was saved for SDS-PAGE analysis of the extraction (SOLUTION 1).

The samples were transferred to high speed centrifuge tubes and centrifuged in a Sorvall RC-5B (TZ-28 rotor) at 18000 RPM for 20 minutes. The supernatant was decanted into a 250 ml conical tube and diluted with an equal volume of Amylose Column Buffer. The mixture was then sterile filtered using a 500 ml 0.45 mm filter unit. The filtered solution contains the cell-free extract (CFE).

Aliquots of SOLUTION 1 and CFE were run on a gel to determine the efficiency of the above procedures. 0.5 ml of SOLUTION 1 was aliquoted into a new eppendorf tube and spun to pellet in the microcentrifuge. The supernatant was discarded and the pellet was resuspended in 0.5 ml of MilliQ water. A 5 ul aliquot of the pellet suspension of SOLUTION 1 along with 5 ul of CFE was run on a 15% SDS-PAGE gel under reducing conditions.

Purification of MBP construct on amylose column:

A 2.5 cm×30 cm HPLC column (Amicon, Beverly, Mass.) was assembled with a Peristaltic Pump (Pharmacia LKB Pump P-1, Piscataway, N.J.), UV Detector (Pharmacia LKB Uvicord SII), and Chart Recorder (Pharmacia LKB Recl). Once the equipment was warmed up (30–60 minutes before use), 60–80 ml of Amylose resin was poured over the column and the column was packed by passing through 4–5 column volumes of MilliQ water. The resin was equilibrated with 2 column volumes of Amylose Column Buffer.

The chart recorder was started and once a stable baseline was achieved, the CFE was loaded using Pump Setting 4 (×10). 100 ml aliquots of the flow through (FT) was collected in 250 ml conical tubes (Corning/VWR, Corning, N.Y.) (Fractions which are collected after the saturation of the column was reached were run over another column) Once the whole CFE had passed the resin, the column was washed with Amylose Column Buffer until the baseline was reached.

Once baseline was achieved, the Amylose Elute Buffer was run through the column. The construct began to elute in the first 3–5 fractions causing a sharp peak to appear on the chromatogram. The fractions were collected until baseline was reattained.

The purity of the peak fractions was determined by running 2–5 ul aliquots of each fraction, varying the amount depending on the strength of the peak (very weak peak requiring more sample), on a 15% SDS-PAGE gel under reducing conditions. The 2 fractions flanking each peak as well as the FT fractions were also run. The FT fractions was run in order to determine if the saturation of the resin was reached. If saturation was reached, the whole flow through or pare of it was run over a second column. If the protein was >90% pure as estimated by SDS-PAGE, the peak fractions were pooled and dialyzed in dialysis membrane of MWCO 25,000 (Spectrum, Los Angeles, Calif.), against four liter volumes of 1× PBS pH 7.2 at 4° C. At least four hours was allowed for each cycle. If significant impurizies were present, SDS-PAGE and Western Blot Analysis were performed on the dialyzed protein.

The Amylose Resin was reused up to five times before losing its binding capacity. Storage of the column was done in 20% Ethanol (Aaper Alcohol, Shelbyville, Ky.) by running 2–3 column volumes through the resin and storing at room temperature.

EXAMPLE 4

PREPARING HIV 1 AND HIV2 IMMOBILIZED ON A TEST ASSAY SURFACE

A porous, nitrocellulose membrane (Millipore 704, 10–20 um, SA3M214H2, nitrocellulose), to which HIV1 and HIV2 antigens were to be attached, was cut into 20 mm squares and placed on a piece of blue interleaf on a benchtop. The front of each square at the bottom center was marked to insure that the blotted side was up and the orientation was clear. The HIV1 antigen was diluted to 8 mg/ml with 0.1N NaOH and the HIV2 antigen was diluted with 0.2 um filtered distilled water (FDW) to 4 mg/ml. An equal volume of HIV2 solution was added to the HIV1 solution and mixed well without foaming (HIV ½ combo-antigen). Protein A (Repligen, RPA-100) was dissolved at 1 mg/ml in FDW for a control. These solutions were prepared fresh and used the same day.

0.5 ul of the HIV ½ protein solution was blotted onto the test assay surface at the bottom center (near the identification mark) and 0.5 ul of the Protein A was blotted at the top center. The blots were spaced in the center of the test assay surface, without any overlap, and allowed to dry for at least 30 minutes at room temperature. The blotted membranes were stored at 4° C. in a zip-lock bag.

EXAMPLE 5

PROCEDURE FOR BLOCKING PREFILTER

A porous, nitrocellulose prefilter membrane (Millipore, HATF 08250, 0.45 um, nitrocellulose) was cut into 20 mm squares, and submerged in PBS containing 5% fetal bovine serum (FBS, JRH#12-10378P) for 20 minutes. The resultant individual filters were then removed from blocking buffer, dipped in PBS to wash off the excess FBS, and transferred to PBS-2% polyethylene glycol (PEG; 3000–3700 MW). Once the filters were removed from the PBS-PEG they were placed on dry filter paper and allowed to dry at least 30 minutes at room Temperature. The membranes were stored at 4° C. in a zip-lock bag.

EXAMPLE 6

PROCEDURE FOR ASSEMBLING DELIVERING MEMBER

A porous diffusing material was formed of a membrane (Millipore 704, 10–20 um, SA3M214H2, nitrocellulose) which was cut into 20 mm squares. Each square was placed on the sticky side of the top half of a two-piece adhesive label, or tab, so as to completely cover a 1.5 cm hole in the label. The top half was marked with typing to distinguish it from the bottom half of the label. The blocked test assay surface membranes from Example 5 were removed from the plastic bag (Millipore, HATF 08250, 0.45 um, nitrocellulose; in some cases Millipore HAHY0000 was used). Each was tamped onto a 1.5 cm hole on the sticky side of the bottom half of the label, which was not marked with any typing. Both membranes were carefully tamped onto the sticky sides of the labels to insure even contact. The labels were carefully stuck together (adhesive sides facing each other) so that the label holes were aligned and then any excess membrane was trimmed off. The label halves thus define a connector, holding the diffusing membrane and prefilter membrane in face to face relation. This assembled delivering member was stored at 4° C. in a zip-lock bag.

EXAMPLE 7

PROCEDURE FOR ASSEMBLING TEST ASSAY KIT

A plastic base having a cavity approximately 0.7 cm deep, 2.1 cm wide and 3.5 cm long was obtained from Porex Technologies. At the bottom of the cavity, a dome approximately 0.3 cm high, with a diameter of approximately 1.5 cm was formed in an upward direction. An urging member in the form of an absorbent material, specifically a cotton ball, was pressed into the cavity of the base so that the cotton was about half an inch above the top of the base. On top of the cotton, was placed one blotted-membrane from Example 4 and on top of that was placed one prefilter (prefilter from Example 6). A plastic cover, also from Porex Technologies, including an opening approximately 1.0 cm in diameter, and forming a well immediately about the opening, was then placed over the membranes so that they were centered within the opening. The top was pressed down and riveted into place. The membrane appeared with a slight "dome" which, when pressed, was very firm, indicating that the device was packed correctly. That is, the test assay surface of the test assay solid phase (blotted membrane of Example 4) was held in even contact with the delivering surface of the delivering member. Similarly, the diffusing membrane and prefilter membrane of the delivering member, held in face to face relation with the label connector of Example 6, were held in even contact according to this arrangement.

EXAMPLE 8

PROCEDURE FOR PRODUCING PROTEIN A LABELED WITH INDIGO

Indigo (Aldrich, 22,929-6) was placed into a mortar and ground with a pestle until the powder was very fine and uniform (about 15 minutes). 1.5 gm of ground Indigo was suspended in 300 ml of milliQ water in a 500 ml Erlenmeyer flask and the solution was heated at 65° C. for 10 minutes. The solution was sonicated for 90 minutes (Branson 450, duty cycle 70, output 4) and then allowed to come to room Temperature (about 90 minutes). The pH of the solution was adjusted to pH 5.5 using 0.1N HCL. 1 mg/ml solution of Protein A (Repligen, RPA-100) was prepared in D-H$_2$O and 1.75 ml was added to 35 ml of the Indigo suspension in a 50 ml tube (Nalgene polypropylene-capped, 8 tubes required). This gave a 50 ug/ml solution. After incubating for 10 minutes at room temperature the solution was centrifuged at 18000 rpm for 50 minutes in an SS34 rotor (Sorvall, RC-5). The supernatant was removed and the pellet was resuspended in 30 ml of 10 mM Na$_2$HPO$_4$, pH 7.4 containing 0.5M NaCl and 1% BSA (PBSBSA). This solution was centrifuged at 18000 rpm for 25 minutes in an SS34 rotor (Sorvall, RC-5) and the pellet was resuspended in 30 ml of PBSBSA containing 10% glycerol (PBSBSAG). The solution was again centrifuged at 18000 rpm for 25 minutes in an SS34 rotor (Sorvall, RC-5) and the pellet was resuspended in 30 ml of PBSBSAG. The solution was filtered through an 8 um filter (Whatman). This took about 20 minutes and resulted in very little loss of material. Then the solution was filtered through a 2 um filter (Whatman). This took about 1 hour and resulted in approximately 30% loss of material. 4 ul of PAI was added to 750 ul of D-H$_2$O and the OD$_{610}$ was adjusted to 0.0075 with PBSBSAG. 1.5 ml of the diluted PAI was aliquoted into vials (Sarstedt, 72730-005) and stored at 4° C.

EXAMPLE 9

PROCEDURE FOR PRODUCING ANTI-IgM-IgG AND ANTI-IgA-IgG LABELED WITH INDIGO 2 g of Indigo (Aldrich, 22,929-6) was placed into a mortar and ground with a pestle until the powder was very fine and uniform (about 15 minutes). 1.5 g of the ground Indigo was suspended in 300 ml of MilliQ water in a 500 ml Erlenmeyer flask, covered with tin foil. The solution was heated at 65° C. for 10 minutes and then allowed to come to room temperature (about 90 minutes). The pH of the solution was adjusted to pH 5.5 using 0.1N HCL. A 450 ug/ml solution of Antibody was prepared as follows: 12 ml Bethyl Goat anti-Human IgA #A920-6 (Affinity Purified) @3.4 mg/ml was added to 16 ml Bethyl Goat anti-Human IgM # M21-6 (Affinity Purified) @2 mg/ml with a total volume of 28 ml and a total of 78 mg. 18 ml of the Indigo suspension was placed into eight 40 ml tubes (Sorvall, 03530) and 3.5 ml of Ab combo was added to each tube, resulting in a 500 ug/ml solution. The solution was then incubated for 30 minutes at room temperature before centrifugation (Sorvall, RC-5 with SS34 rotor) at 18000 rpm for 50 minutes. The supernatant was removed and the pellet was resuspended in 18 ml of 10 mM Na$_2$HPO$_4$ (Sigma), pH 7.4 containing 0.5M NaCl (Sigma) and 1% BSA (Miles, Pentax, Fract V, 81003-40 [PBSBSA]). This solution was centrifuged at 18000 rpm for 25 minutes in an SS34 rotor (Sorvall, RC-5) with the brake off. The pellet was resuspended in 18 ml of PBSBSA containing 10% glycerol (Amresco, 0854) (PBSBSAG). This solution was again centrifuged at 18000 rpm for 25 minutes in an SS34 rotor (Sorvall, RC-5) with the brake off, and the pellet was resuspended in 18 ml of PBSBSAG. The solution was filtered through an 8 um filter (S&S immobilization membrane, #AE99), followed by a 5 um filter (MSI, magna nylon transfer membrane), then a 2 um filter (Millipore, Immobilion AV-2, SA3J898E8). The OD of the solution was checked by measuring at 610 nm. 8 ul of Ab-I was added to 1.5 ml PBSBSAG and the OD was adjusted to 0.03 with PBSBSAG. For example, if the 8 ul gave an OD of 0.12 the PAI was diluted 1:4 with PBSBSAG. NaN$_3$ was added to a final concentration of ug/ml and the solution was stored at 4° C.

EXAMPLE 10

PROCEDURE FOR PRODUCING DETECTION REAGENT 15.6 mls of IMA (Solution obtained in Example 9) was mixed with 109.4 mls of IPA (Solution obtained in Example 8). 375 mls of PBSBSAG containing 40 ug/ml of NaN$_3$ was added to this solution. The total volume was 500 mls and the solution had an OD$_{610}$=0.015. 500 mls of PBSBSAG containing 40 ug/ml of NaN$_3$ was added and the final solution had an OD$_{610}$=0.0075.

EXAMPLE 11

PROCEDURE FOR PRODUCING PROTEIN A,

ANTI-IgA, ANTI-IgM-PIGMENT DETECTOR 100 mg of pigment, either Red 17=part #235-7515; Violet 23=part #246-1670 or Green 7=part #264-3120; from Sun Chemical, 4526 Chickering Avenue, Cincinnati, Ohio 45232, was measured out and placed into a 50 ml conical tube (Sarstedt). One of the following was added to the tube containing the pigment: 1) 20 ml of a 1 mg/ml-distilled water solution of Protein A (RPA-100, Repligen), 2) 6 ml of Goat anti-Human IgA (A80-102A, Lot A92G, 3.4 mg/ml, Bethyl Labs, Montgomery, Tex.), or 3) 8 ml of Goat anti-Human IgM (A80-100A, Lot M121G, 2.0 mg/ml, Bethyl Labs). The material in each vial was suspended by inversion but it was done with care so as not to create too much foam (about 30 minutes). The suspension which was clumpy and not well suspended contained fluid which was clear and did not take on the color of the pigment. Each tube was brought to a final volume of 45 ml by adding PBSBSAG (10 mM Na2HP04, 0.5M NaC), 1% BSA:#81003-40, Miles, Pentax, 10% Glycerol:#0854-1, Amresco). The material in each vial was suspended by inversion and by crushing the clumps with a stainless-steel spatula, while taking care not to create too much foam (approx 15 minutes). The suspension which started to take on the color of the pigment but which was still clumpy and not well suspended, was incubated at room temperature for 45 minutes, and then centrifuged at 18000 rpm for 25 minutes, with the brake off (Sorvall, RC-5 centrifuge, SS34 rotor using 50 ml tubes, Sorvall, #03530). The supernatant was removed and the was pellet resuspend in 100 ml PBSBSAG. The suspension was first filtered through an 8 um filter (S&S, AE99) and then through a 2 um filter (Milliport. Immobilion AV-2, SA31898E8). NaN3 was then added to the solution to a final concentration of 20 ug/ml.

EXAMPLE 12

TEST ASSAY 120 ul of a serum sample was added directly onto the center of the delivering member of the test assay kit of the present invention. After from 10 to 15 seconds, the delivering member was removed and discarded. 1.5 ml (0.015 OD units) of the detection reagent of Example 10 was added into the well and allowed to flow through the membrane (about 10 seconds). The results were recorded.

EXAMPLE 13

COMPARATIVE POSITIVE, NEGATIVE, AND ERROR RESULTS USING AN ASSAY KIT 120 ul of each of a positive and negative HIV serum sample was added to the center of a delivering member of a test assay kit prepared in accordance with the present invention. After from 10 to 15 seconds, in each case, the prefilter was removed and discarded. In each case, 1.5 ml of the detection reagent prepared in accordance with Example 10 was added into the assay kit well and allowed to flow through The test assay membrane, which was completed in about 10 seconds. FIG. 2c illustrates the appearance of the test assay surface to which a positive serum sample had been applied, following the application of the detection reagent. FIG. 2b illustrates the appearance of the test assay surface to which a negative serum sample had been applied, after application of the detection reagent. As a comparative (error) example, the prefilter was removed from a test assay kit prepared in accordance with Example 10 and the test assay surface was wetted unevenly with a negative serum sample. That is, a portion of the test assay surface was contacted with serum to a greater extent than another portion. Subsequently, 1.5 ml of the detection reagent prepared in accordance with Example 10 was added allowed to flow through The test assay membrane. The results are illustrated in FIG. 2a. The unevenness of the distribution of the label on the Test assay surface can be measured with the naked eye, indicating the unevenness of the serum application to the Test assay surface.

The preceding examples are set forth to illustrate the specific embodiments of the invention and are not intended to limit the scope of the invention. Additional embodiments and advantages within the scope of the claimed invention will be apparent to those of ordinary skill in the art.

What is claimed is:

1. A test assay kit comprising a package containing:
   a test assay surface for supporting a test assay reaction and including a binding partner of a test assay analyte immobilized thereupon;
   a porous cellulosic prefilter having a pore size of from about 0.1 to about 1.0 microns, and having a delivering surface positionable in face to face relation with the test assay surface and a sample receiving surface opposite the delivering surface, the prefilter being removable from the test assay surface; and
   a surfactant on the prefilter sample receiving surface, wherein the prefilter, except at the receiving surface, is essentially free of the surfactant.

2. The test assay kit as recited in claim 1, wherein the prefilter has a thickness from about 50 to about 300 microns.

3. The test assay kit as recited in claim 1, wherein the prefilter and diffusing material are constructed and arranged as a delivering member that is removable from the test assay surface during a test assay for determination of an analyte.

4. The test assay kit as recited in claim 1, wherein the test assay surface carries an immobilized binding partner of an analyte.

5. The test assay kit as recited in claim 1, wherein the test assay surface includes a first area carrying an immobilized binding partner of a labeled reagent, and a second area having a chemical functionality allowing non-specific binding of a labeled reagent at a detectable level distinguishable from binding of labeled reagent to the immobilized binding partner, the second area allowing non-specific binding of labeled reagent to a first degree when a sample is first applied to the second area to a first extent, and non-specific binding of labeled reagent to a second degree, distinguishable from the first degree, when a sample is first applied to the second area to a second extent different from the first extent.

6. The test assay kit as recited in claim 1, wherein the prefilter delivering surface is positioned in even contact with the test assay surface.

* * * * *